United States Patent
Watanabe et al.

(10) Patent No.: US 11,529,096 B2
(45) Date of Patent: Dec. 20, 2022

(54) SLEEP ASSESSMENT SYSTEM, MASSAGE SYSTEM, CONTROL METHOD, AND ELECTRONIC DEVICE

(71) Applicant: KYOCERA Corporation, Kyoto (JP)

(72) Inventors: Takahiro Watanabe, Yokohama (JP); Osamu Tochikubo, Yokohama (JP)

(73) Assignee: KYOCERA CORPORATION, Kyoto (JP)

( * ) Notice: Subject to any disclaimer, the term of this patent is extended or adjusted under 35 U.S.C. 154(b) by 85 days.

(21) Appl. No.: 16/651,807

(22) PCT Filed: Sep. 28, 2018

(86) PCT No.: PCT/JP2018/036593
§ 371 (c)(1),
(2) Date: Mar. 27, 2020

(87) PCT Pub. No.: WO2019/066075
PCT Pub. Date: Apr. 4, 2019

(65) Prior Publication Data
US 2020/0237294 A1    Jul. 30, 2020

(30) Foreign Application Priority Data

Sep. 29, 2017    (JP) .............................. JP2017-191743

(51) Int. Cl.
| | |
|---|---|
| *A61B 5/00* | (2006.01) |
| *A61B 5/0205* | (2006.01) |
| *A61H 7/00* | (2006.01) |
| *A61M 21/00* | (2006.01) |

(Continued)

(52) U.S. Cl.
CPC .......... *A61B 5/4812* (2013.01); *A61B 5/0205* (2013.01); *A61B 5/4809* (2013.01); *A61B 5/4836* (2013.01); *A61B 5/6817* (2013.01); *A61B 5/7278* (2013.01); *A61B 5/7405* (2013.01); *A61B 5/746* (2013.01); *A61H 7/00* (2013.01); *A61M 21/00* (2013.01); *A61B 5/026* (2013.01); *A61B 5/369* (2021.01); *A61M 2021/0083* (2013.01)

(58) Field of Classification Search
CPC ....... A61B 5/4806–4815; A61B 5/6814–6817; A61M 21/00; A61M 2021/0083; A61H 7/00
See application file for complete search history.

(56) References Cited

U.S. PATENT DOCUMENTS

| | | | |
|---|---|---|---|
| 9,668,657 B2 | 6/2017 | Takahashi | |
| 10,004,873 B1 * | 6/2018 | Hur ...................... | A61B 5/6893 |
| 10,183,142 B2 * | 1/2019 | Garcia Molina .... | A61B 5/4812 |

(Continued)

FOREIGN PATENT DOCUMENTS

| | | |
|---|---|---|
| CN | 105377129 A | 3/2016 |
| CN | 105640703 A | 6/2016 |

(Continued)

*Primary Examiner* — Carl H Layno
*Assistant Examiner* — Manolis Pahakis
(74) *Attorney, Agent, or Firm* — Volpe Koenig

(57) ABSTRACT

A sleep assessment system includes a blood flow measurement unit and a assessment unit. The blood flow measurement unit acquires first information related to the blood flow of the user. The assessment unit determines the sleep stage of the user based on the first biological information.

16 Claims, 37 Drawing Sheets

(51) Int. Cl.
*A61B 5/026* (2006.01)
*A61B 5/369* (2021.01)

(56) References Cited

U.S. PATENT DOCUMENTS

| | | | |
|---|---|---|---|
| 10,363,388 B2* | 7/2019 | Fonseca | A61B 5/0295 |
| 11,229,397 B2* | 1/2022 | Garcia Molina | A61B 5/4848 |
| 11,266,807 B2* | 3/2022 | Garcia Molina | A61B 5/4836 |
| 2006/0106275 A1* | 5/2006 | Raniere | A61M 21/02 600/26 |
| 2007/0083079 A1* | 4/2007 | Lee | A61B 5/4812 600/27 |
| 2008/0234785 A1 | 9/2008 | Nakayama et al. | |
| 2010/0087701 A1* | 4/2010 | Berka | A61M 21/02 600/27 |
| 2010/0217100 A1* | 8/2010 | LeBoeuf | G02B 6/0001 600/301 |
| 2011/0021866 A1* | 1/2011 | Iizuka | A61B 5/024 600/26 |
| 2012/0197093 A1* | 8/2012 | LeBoeuf | A61B 5/026 600/301 |
| 2012/0251989 A1* | 10/2012 | Wetmore | G09B 19/00 434/236 |
| 2013/0102939 A1* | 4/2013 | Sudarev | A61H 9/0078 601/151 |
| 2013/0131519 A1* | 5/2013 | LeBoeuf | A61B 5/0059 600/476 |
| 2013/0190556 A1* | 7/2013 | Wetmore | A61M 21/00 600/27 |
| 2014/0057232 A1* | 2/2014 | Wetmore | G09B 19/00 600/28 |
| 2014/0210626 A1* | 7/2014 | Kresser | A61M 21/00 340/575 |
| 2014/0278229 A1* | 9/2014 | Hong | A61B 5/486 702/160 |
| 2016/0007916 A1 | 1/2016 | Iwawaki | |
| 2016/0015314 A1* | 1/2016 | Dusanter | A61B 5/4818 600/301 |
| 2016/0015315 A1* | 1/2016 | Auphan | A61B 5/6892 600/301 |
| 2016/0045706 A1* | 2/2016 | Garcia Molina | A61M 21/02 600/27 |
| 2016/0082222 A1 | 3/2016 | Garcia Molina et al. | |
| 2016/0089059 A1* | 3/2016 | Hu | A61B 5/7207 600/595 |
| 2016/0310696 A1* | 10/2016 | Fonseca | A61B 5/4812 |
| 2017/0094046 A1 | 3/2017 | Raymann et al. | |
| 2017/0164847 A1* | 6/2017 | Pande | A61B 5/0002 |
| 2017/0164893 A1* | 6/2017 | Narayan | A61B 5/14539 |
| 2018/0177975 A1* | 6/2018 | Goto | A61B 5/4809 |
| 2018/0184969 A1 | 7/2018 | Zhao et al. | |
| 2019/0001117 A1* | 1/2019 | Ben-David | A61B 5/4812 |
| 2021/0169417 A1* | 6/2021 | Burton | A61B 5/4857 |
| 2022/0218293 A1* | 7/2022 | Chou | A61B 5/6804 |

FOREIGN PATENT DOCUMENTS

| | | |
|---|---|---|
| CN | 106540367 A | 3/2017 |
| JP | 2001-120626 A | 5/2001 |
| JP | 2001-190616 A | 7/2001 |
| JP | 2003-275317 A | 9/2003 |
| JP | 2003-339809 A | 12/2003 |
| JP | 2005-074115 A | 3/2005 |
| JP | 2008-229248 A | 10/2008 |
| JP | 2010-018055 A | 1/2010 |
| JP | 2012-065853 A | 4/2012 |
| JP | 2015-109964 A | 6/2015 |
| JP | 2016-014542 A | 1/2016 |
| JP | 2016-016203 A | 2/2016 |
| JP | 2017-018772 A | 1/2017 |
| WO | 2008/029399 A2 | 3/2008 |
| WO | 2015/194163 A1 | 12/2015 |

* cited by examiner

FIG. 28

10001: • Individual ID | • Date and time | Second information | Fifth information | Sixth information 10002: • Individual ID | Sex | Age | Occupation

SLEEP ASSESSMENT SYSTEM, MASSAGE SYSTEM, CONTROL METHOD, AND ELECTRONIC DEVICE

CROSS-REFERENCE TO RELATED APPLICATION

The present application claims priority to and the benefit of Japanese Patent Application No. 2017-191743 filed Sep. 29, 2017, the entire contents of which are incorporated herein by reference.

TECHNICAL FIELD

The present disclosure relates to a sleep assessment system, a massage system, a control method, and an electronic device.

BACKGROUND

An apparatus for awakening a person based on the sleep state of the person is known. Need for determining the sleep state of a person therefore exists.

SUMMARY

A sleep assessment system according to an aspect of the present disclosure includes a blood flow measurement unit and a controller. The blood flow measurement unit acquires first biological information related to the blood flow of the user. The controller determines the sleep stage of the user based on the first biological information.

A massage system according to an aspect of the present disclosure includes a sleep assessment system and a massage unit. The controller determines a timing of a massage by the massage unit based on the first biological information of the sleep assessment system.

A control method according to an aspect of the present disclosure includes acquiring first biological information related to the blood flow of a user and determining the sleep stage of the user based on the first biological information.

An electronic device according to an aspect of the present disclosure includes a sleep assessment system or a massage system.

BRIEF DESCRIPTION OF THE DRAWINGS

In the accompanying drawings:

FIG. 28 is a conceptual diagram of the data structure of data stored on the server 50 of FIG. 25;

DETAILED DESCRIPTION (Sleep Assessment System)

Embodiment

Figure 1:
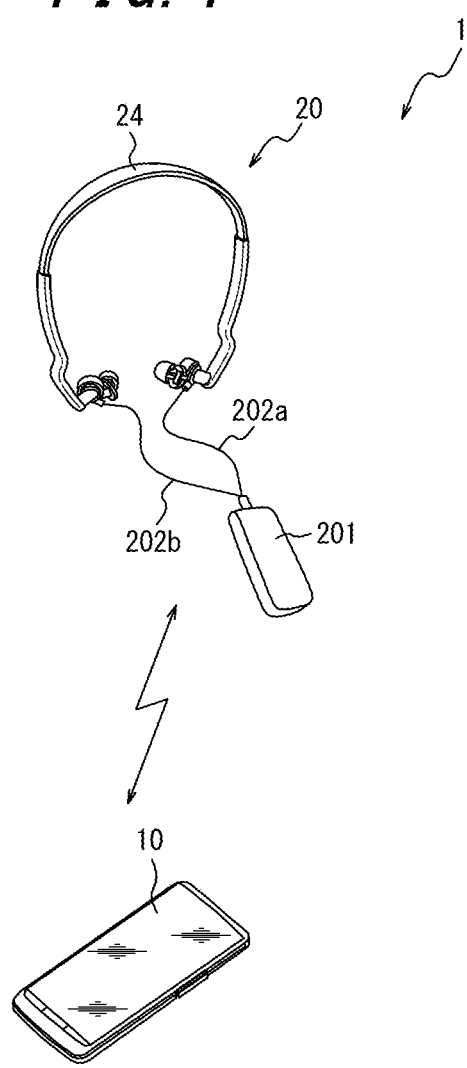
FIG. 1 illustrates the configuration of an embodiment of a sleep assessment system 1 according to the present disclosure.

FIG. 1 schematically illustrates the configuration of a sleep assessment system 1 according to an embodiment.

The sleep assessment system 1 includes an information processing apparatus 10 and a blood flow measurement apparatus 20. Consequently, the sleep assessment system 1 can determine the sleep stage of a user who is using the sleep assessment system 1.

An electroencephalograph has been used to measure sleep states. Measurement with an electroencephalograph, however, requires highly specialized skill and knowledge. An electroencephalograph is also extremely complicated to wear, making simple measurement difficult. By contrast, the sleep state of a user is, for example, determined based on information related to the user's blood flow in the present disclosure. This allows the sleep state to be determined more easily than with known methods.

The information processing apparatus 10 can control the sleep assessment system 1. The information processing apparatus 10 includes a control unit 11, a storage 12, an input interface 13, a display 14, and a communication interface 15. The control unit 11 further includes a assessment unit 17 that determines the sleep state of a user.

The control unit 11 can control and manage the information processing apparatus 10. The control unit 11 includes at least one processor 11a that controls and manages the functional blocks of the information processing apparatus 10. The functions of the control unit 11 are implemented by the at least one processor 11a, which is a CPU or the like that executes a program prescribing control procedures. Such a program may, for example, be stored in the storage 12 or on an external storage medium or the like connected to the information processing apparatus 10.

The at least one processor 11a may be implemented as a single integrated circuit (IC) or as a plurality of communicatively connected integrated circuits and/or discrete circuits. The at least one processor 11a can be implemented with a variety of known techniques.

The processor 11a includes one or more circuits or units configured to execute one or more data calculation procedures or processes by executing instructions stored in related memory, for example. The processor 11a may also be firmware configured to execute one or more data calculation procedures or processes. The firmware may, for example, include a discrete logic component.

The processor 11a may include one or more processors, controllers, microprocessors, microcontrollers, application specific integrated circuits (ASIC), digital signal processors, programmable logic devices, field programmable gate arrays, any combination of these devices or structures, or a combination of other known devices or structures.

The storage 12 can, for example, store various information and/or programs for operating the information processing apparatus 10. The storage 12 can be configured by a semiconductor memory, a magnetic memory, or the like. The storage 12 may also function as a working memory.

The input interface 13 transmits an input signal based on input from the user to the control unit 11. The input interface 13 may, for example, be an operation button or a touch panel. The input interface 13 may, for example, be an operation button that controls the power of the information processing apparatus 10 to be on or off.

The display 14 displays images for operation of the information processing apparatus 10. The display 14 is a display device constituted by a well-known display, such as a liquid crystal display (LCD), an organic electro-luminescence display (OELD), or an inorganic electro-luminescence display (IELD). The display 14 may be a touch panel that functions as an input region for accepting operation input of the input interface 13.

The communication interface 15 can transmit and receive various information to and from each apparatus forming part of the sleep assessment system 1 and/or the outside. The communication interface 15 can transmit and receive information using a network that is wireless, wired, or a combination of wireless and wired. The communication interface 15 can, for example, communicate with Bluetooth® (Bluetooth is a registered trademark in Japan, other countries, or both), infrared, NFC, wireless LAN, wired LAN, any other communication medium, or any combination of these.

The information processing apparatus 10 may, for example, be a desktop PC, a tablet PC, or a terminal device such as a smartphone. The information processing apparatus 10 is connected via the communication interface 15 to the blood flow measurement apparatus 20 in a wireless, wired, or combination wireless/wired manner to allow communication of information.

The blood flow measurement apparatus 20 is an apparatus for performing measurement at a measured part to acquire first information of the measured part (first biological information). The first information is information related to blood flow. The information related to blood flow may, for example, be data of an electric signal, optical signal, or the like that varies based on changes in blood flow, such as changes in the blood flow rate or changes in the oxygen concentration of the blood. The first information becomes biological information used to perform various calculations or control in the information processing apparatus 10.

The blood flow measurement apparatus 20 includes a blood flow measurement unit 24 and a controller 201. The blood flow measurement unit 24 includes a sensor for acquiring the first information. The controller 201 can control the blood flow measurement apparatus 20. The blood flow measurement unit 24 and the controller 201 may be connected in a wired manner, such as by a cable, in a wireless manner, or in a combined wired/wireless manner. In the present embodiment, the blood flow measurement unit 24 and the controller 201 are connected by cables 202a, 202b and transmit and receive information and/or power.

In the present embodiment, second information can be further calculated from the first information by the information processing apparatus 10. The second information is data yielded by performing calculations on the first information. For example, the second information is a blood flow rate, blood flow wave height, heartbeat interval, volume pulse wave, or acceleration pulse wave. The blood flow rate is the rate of the blood flow per unit time at a measured part. The blood flow wave height is the difference between the maximum and minimum values of the blood flow rate during one heartbeat and serves as an index of vasodilatation. The heartbeat interval is the interval between heartbeats and serves as an index of whether the user is relaxed. The volume pulse wave is a waveform representation of the change in blood flow rate due to a heartbeat. The volume pulse wave serves as an index of blood vessel expansion and contraction. The acceleration pulse wave is a waveform representation of the value obtained as the second derivative, with respect to time, of the blood flow rate represented as the volume pulse wave.

Figure 2:
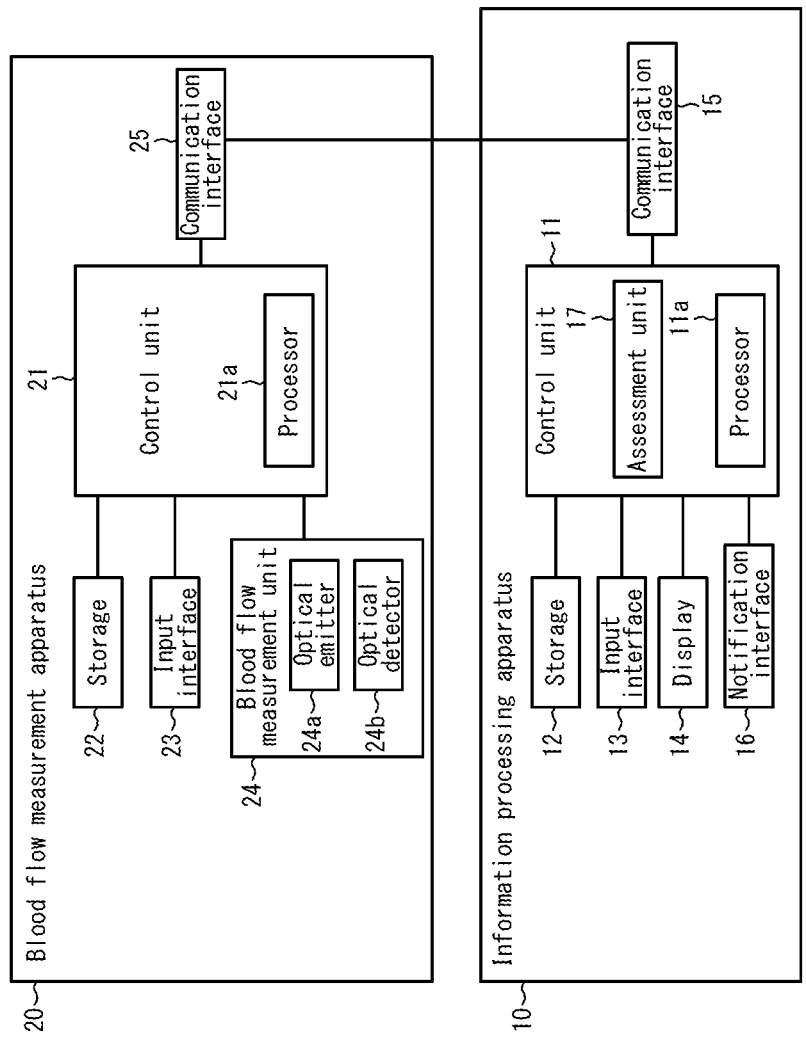
FIG. 2 is a functional block diagram illustrating the schematic configuration of the sleep assessment system 1 of FIG. 1.

FIG. 2 is a functional block diagram illustrating the schematic configuration of the sleep assessment system 1 of FIG. 1.

The blood flow measurement apparatus 20 is described in greater detail below.

The blood flow measurement apparatus 20 can obtain the first information from a portion of the user's body. When measurement is to be performed at the user's ear, the blood flow measurement apparatus 20 can be configured as an earplug-type apparatus that has an arched headband (FIG. 1). In this case, the blood flow measurement apparatus 20 may be worn on the user's head, for example, and the earpiece inserted in the ear (external ear canal).

The configuration of the blood flow measurement apparatus 20 is not limited to the above example, as long as information related to blood flow can be acquired. The blood flow measurement apparatus 20 may, for example, be an earplug-type apparatus without a headband. The blood flow measurement apparatus 20 may also have any other configuration appropriate for the measured part. For example, the blood flow measurement apparatus 20 may be a finger cot, clip, cuff, or ring-type apparatus. The measured part is therefore not limited to the ear and may be any site allowing measurement of the blood flow. For example, the measured part may be a finger, wrist, arm, or leg.

Figure 3:
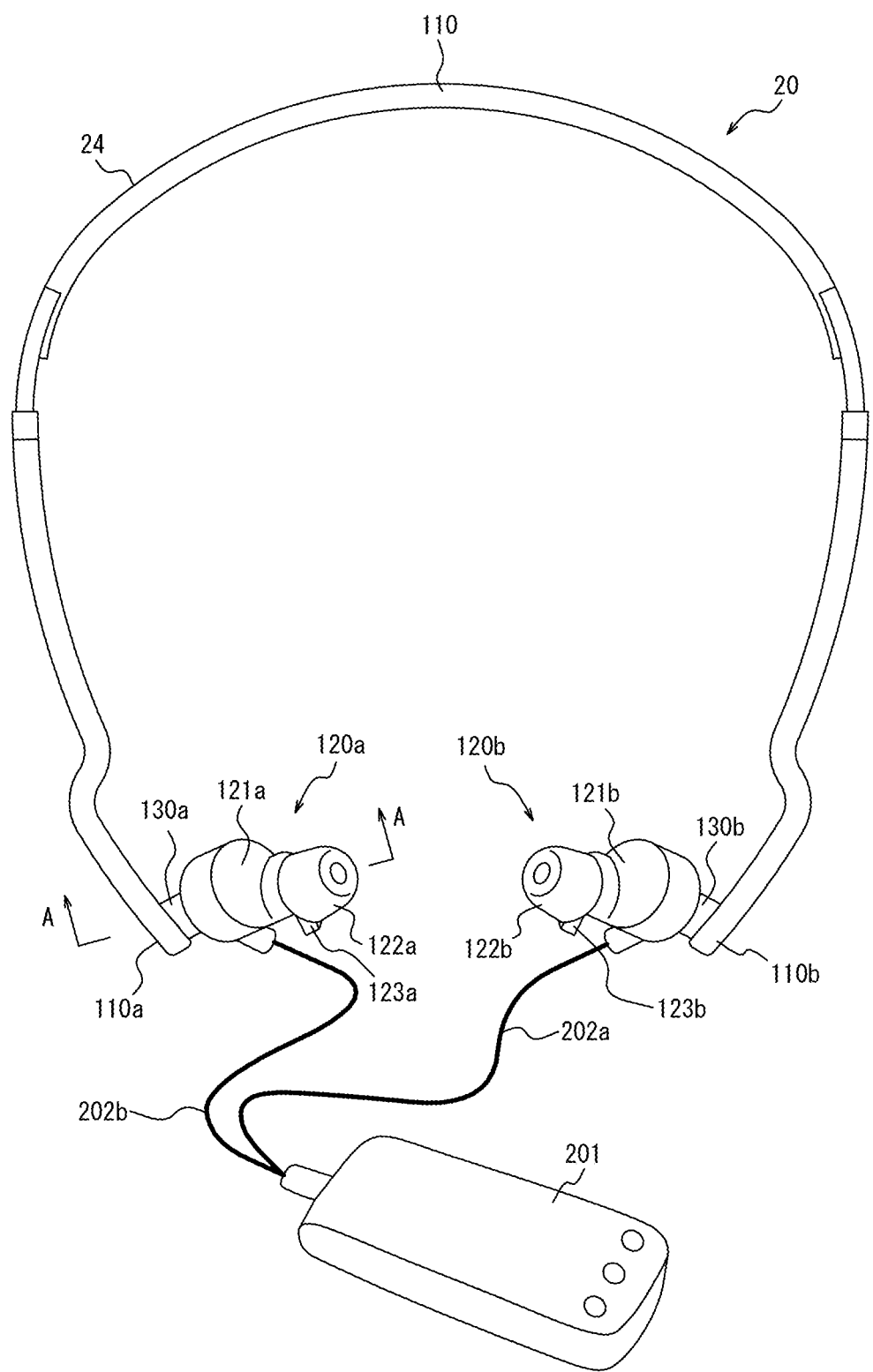
FIG. 3 is a more detailed schematic view of a blood flow measurement apparatus 20 of FIG. 1.
Figure 4:
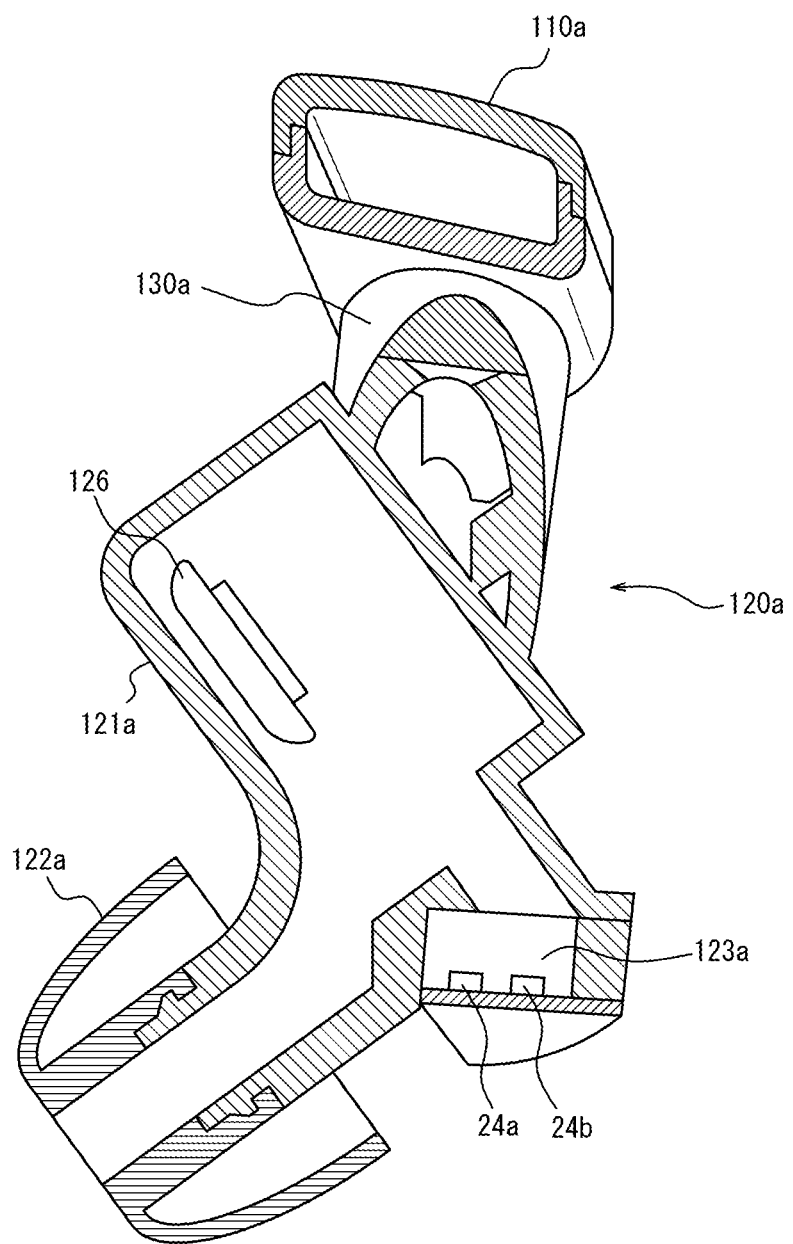
FIG. 4 is a cross-sectional diagram illustrating a portion of the blood flow measurement apparatus 20 of FIG. 3.

FIG. 3 is a schematic view of the appearance of the blood flow measurement apparatus 20 illustrated in FIG. 1, and FIG. 4 is a cross-sectional view of the blood flow measurement apparatus 20 of FIG. 3. In FIG. 4, details of a portion of the internal configuration of the blood flow measurement apparatus 20 are omitted.

The blood flow measurement apparatus 20 of the present embodiment can measure the blood flow of a subject while the blood flow measurement unit 24 is worn by the subject. The blood flow measurement unit 24 can, for example, be worn on the head of the subject. The blood flow measurement unit 24 of the present embodiment includes a wearing portion 110, a measurement unit 120, and connectors 130.

In the present disclosure, the blood flow measurement unit 24 is described as being used while worn on the head of the subject. Lowercase letters are omitted when left and right are not distinguished between.

The wearing portion 110 is a mechanism for maintaining the blood flow measurement unit 24 in a state of being worn by the subject. The wearing portion 110 may, for example, be shaped as an arch or cap. In the present embodiment, the wearing portion 110 is shaped as an arch (FIG. 3). Since the wearing portion 110 is shaped as an arch, the subject can wear the blood flow measurement unit 24 by fitting the wearing portion 110 onto his head. The wearing portion 110 may, for example, include a mechanism for adjusting the length of the wearing portion 110 to match the size of the subject's head. The wearing portion 110 may, for example, be made of synthetic resin, metal, or the like.

The measurement unit 120 can measure blood flow. The measurement unit 120 of the present embodiment is disposed in an end 110 of the wearing portion 110. Specifically, the measurement unit 120 is connected to the wearing portion 110 via the connector 130. The connector 130 is positioned in a portion connecting the measurement unit 120 to the end 110 of the wearing portion 110.

The measurement unit 120 of the present embodiment can, in particular, measure blood flow in the ear of the user. The measurement unit 120 includes a case 121, an earpiece 122, and a sensor unit 123. The earpiece 122 is inserted inside the external ear canal of the subject's ear when the subject is wearing the blood flow measurement apparatus 20. Consequently, the measurement unit 120 can measure the blood flow in the concha auriculae of the ear, for example.

The case 121 is a case for protecting components disposed therein. In the present embodiment, the case 121 functions as a case for protecting a sensor included in the sensor unit 123. The case 121 is, for example, made of synthetic resin, metal, or the like.

The earpiece 122 is disposed so as to surround the tip of the case 121. The earpiece 122 is, for example, made of silicone, sponge, urethane, or the like. The earpiece 122 is shaped to be insertable in the external ear canal.

The sensor unit 123 can transmit and receive signals related to the measured part. The sensor unit 123 includes an optical emitter 24a and an optical detector 24b. The sensor unit 123 is positioned to be in contact with the concha auriculae, which is the measured part, when the earpiece 122 is inserted in the external ear canal. While inserted in the external ear canal, the earpiece 122 can maintain the contact state of the sensor unit 123a with respect to the concha auriculae, which is the measured part. As long as the blood flow measurement apparatus 20 functions properly, the sensor unit 123 is not necessarily required to be in contact with the measured part.

The optical emitter 24a emits light. For example, the optical emitter 24a irradiates the measured part with light (measurement light) of a wavelength capable of detecting a predetermined component included in blood. The optical emitter 24a of the present embodiment is, for example, configured by at least one laser diode (LD).

The optical detector 24b can detect scattered light that is scattered by the measured part among the irradiated measurement light. The optical detector 24b can convert a detected optical signal to an electric signal. The optical detector 24b is, for example, configured by at least one photodiode (PD).

The controller 201 of the present embodiment includes a control unit 21, a storage 22, an input interface 23, and a communication interface 25. The controller 201 may be provided as a separate body from the blood flow measurement unit 24, as illustrated in FIG. 2. While not illustrated, the controller 201 may instead be integrated with the blood flow measurement unit 24. In other words, each functional component of the controller 201 may be provided inside the case 121, and the functions of the blood flow measurement unit 24 and the controller 201 may be unified. It is also possible to provide only the necessary structure of the controller 201 inside the case 121.

The control unit 21 can control the sensor unit 123. Specifically, the control unit 21 can control emission of light by the optical emitter 24a of the sensor unit 123. The control unit 21 of the blood flow measurement apparatus 20 can also execute processing to measure the first information of the user in response to a signal received from the blood flow measurement unit 24 of the blood flow measurement apparatus. Specifically, the control unit 21 can acquire the first information of the measured part based on an output signal from the optical detector 24b. An example of the blood flow measurement apparatus 20 acquiring first information related to the blood flow rate based on the Doppler effect is described below.

When the light irradiated by the optical emitter 24a is scattered by blood flowing inside body tissue, the frequency shifts due to the Doppler effect (Doppler shift). The Doppler shift depends on the speed at which blood flows. The control unit 21 detects a beat signal that occurs due to light interference between the scattered light from still tissue (i.e. scattered light with no Doppler shift) and the scattered light from flowing blood (i.e. scattered light with a Doppler shift). The beat signal is represented as the change over time in the signal intensity. The control unit 21 generates a power spectrum based on the beat signal. The power spectrum is a frequency spectrum representing the signal intensity of the beat signal at a certain time for each frequency component. In the power spectrum, the intensity at each frequency changes depending on the speed at which blood flows. The control unit 21 calculates a value by integrating the power spectrum. In other words, the first information in the present embodiment is, for example, an integral value of the power spectrum.

In the above example, the blood flow measurement apparatus 20 acquires the first information based on the Doppler effect, but the first information may be acquired based on a different physical phenomenon. For example, the blood flow measurement apparatus 20 may be a photoelectric blood flow meter based on absorbance or an ultrasonic blood flow meter based on the Doppler effect of ultrasonic waves.

The control unit 21 includes at least one processor 21a that controls and manages the blood flow measurement apparatus 20 overall, starting with the functional blocks of the blood flow measurement apparatus 20. The functions of the control unit 21 are implemented by the at least one processor 21a, which is a CPU or the like that executes a program prescribing control procedures. Such a program may, for example, be stored in the storage 22 or on an external storage medium or the like connected to the blood flow measurement apparatus 20. The processor 21a may have the same configuration as the above-described processor 11a.

The storage 22 can, for example, store various information and/or programs for operating the blood flow measurement apparatus 20. The storage 22 can be configured by a semiconductor memory, a magnetic memory, or the like. The storage 22 may also function as a working memory.

The input interface 23 can receive input from the user. The input interface 23 may, for example, be an operation button or a touch panel. The input interface 23 may, for example, be an operation button that controls the power of the blood flow measurement apparatus 20 to be on or off.

The communication interface 25 can transmit and receive various information to and from each apparatus forming part of the sleep assessment system 1 and to and from the outside. Consequently, the communication interface 25 can transmit the first information to the information processing apparatus 10 via the communication interface 15. The blood flow measurement apparatus 20 can also receive information from the outside by communicating with the information processing apparatus 10 via the communication interface 15 and the communication interface 25. The specific configuration of the communication interface 25 and its method for transmitting and receiving information may be similar to those of the communication interface 15.

Next, an example of processing executed by the sleep assessment system 1 to determine the sleep state is described together with information processing executed by the information processing apparatus 10.

Figure 5:
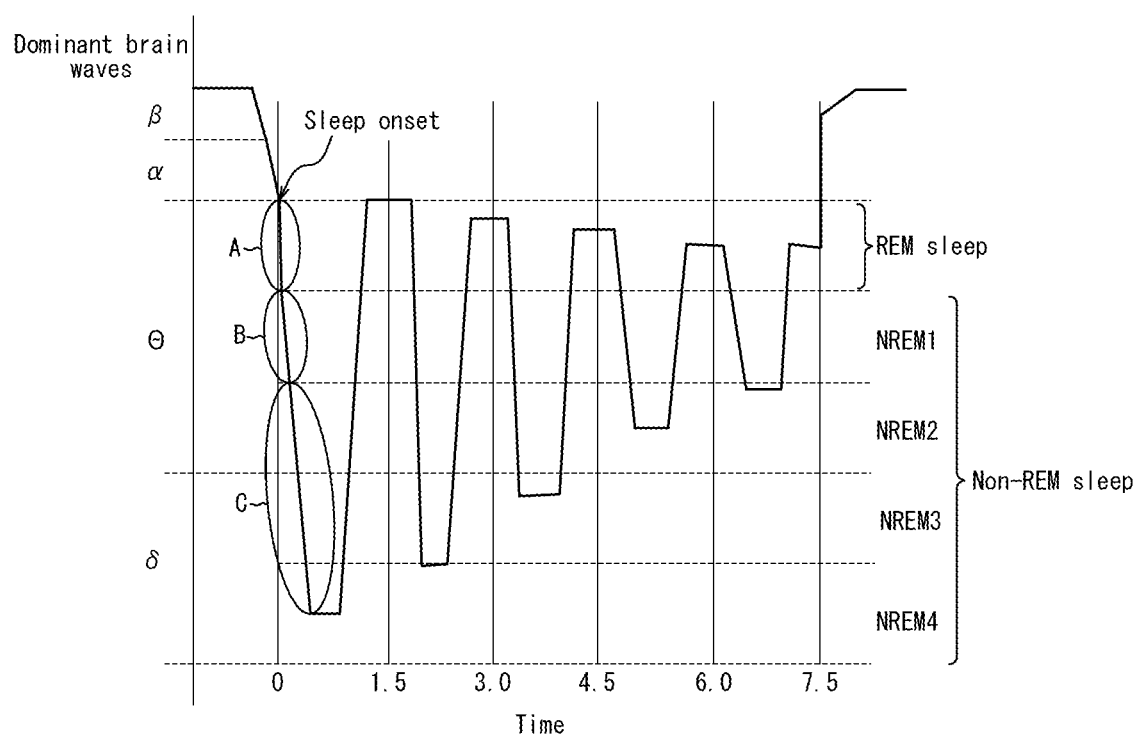
FIG. 5 schematically illustrates an example of sleep-related brain waves.

FIG. 5 schematically illustrates an example of sleep-related brain waves. FIG. 5 illustrates the change in sleep-related brain waves and the type of dominant brain waves.

Brain waves are divided into four types, starting from longer wavelength: $\beta$ waves, $\alpha$ waves, $\theta$ waves, and $\delta$ waves. $\beta$ waves are, for example, brain waves in a frequency range of 38 Hz to 14 Hz. $\alpha$ waves are, for example, brain waves in a frequency range of 14 Hz to 8 Hz. $\theta$ waves are, for example, brain waves in a frequency range of 8 Hz to 4 Hz. $\delta$ waves are, for example, brain waves in a frequency range of 4 Hz to 0.5 Hz.

When $\theta$ waves or $\delta$ waves are dominant compared to $\beta$ waves or $\alpha$ waves, people are asleep. Here, "dominant" refers to a large ratio of certain waves among measured brain waves. It is known that the frequency of brain waves changes cyclically in the range of $\theta$ waves and $\delta$ waves during sleep (FIG. 5). Furthermore, people are in rapid eye movement (REM) sleep when the ratio of $\theta$ waves included in brain waves is less than a predetermined ratio and are in non-rapid eye movement (non-REM) sleep when the ratio of $\theta$ waves is equal to or greater than a predetermined ratio and when $\delta$ waves are dominant (FIG. 5).

Non-REM sleep is sleep without rapid eye movements. REM sleep is sleep with rapid eye movements.

Non-REM sleep is further classified by the depth of sleep. Non-REM sleep may be classified in order of increasing depth as NREM1, NREM2, NREM3, and NREM4 (FIG. 5). Non-REM sleep may be classified into any number of stages, such as three or five.

The assessment unit 17 of the information processing apparatus 10 can determine the sleep stage. The sleep stage changes during the transition to REM sleep or non-REM sleep, for example. As described above, the sleep state has a predetermined correlation with brain waves. The second information also has a predetermined correlation with brain waves. Therefore, the assessment unit 17 can infer the sleep stage based on the second information.

An algorithm for determining the sleep state based on the second information may be stored in advance in the storage 12, for example. In this case, a relationship table between the second information and brain waves may be stored in advance in the storage 12. The brain waves used in the relationship table need not be the actual user's own brain waves as long as they correlate with the user.

Specifically, the information processing apparatus 10 may determine the sleep stage based on the second information corresponding to the brain waves. In other words, the information processing apparatus 10 acquires the ratio of $\theta$ waves and/or $\delta$ waves based on the second information. Based on the ratio of $\theta$ waves and/or $\delta$ waves, the information processing apparatus 10 may then determine a transition in the sleep stage, such as from NREM1 to NREM2 or from NREM4 to NREM3.

Biological activity exhibits different behavior during wakefulness and during sleep. Accordingly, the sleep assessment system 1 can also determine sleep onset and wakefulness of the user based on the second information. Specifically, the information processing apparatus 10 acquires the ratio of α waves and θ waves based on the second information. Next, the information processing apparatus 10 can determine that the user is wakeful when α waves are more dominant than θ waves. Conversely, the information processing apparatus 10 can determine that sleep onset has occurred, i.e. that the user has fallen asleep, when θ waves are more dominant than α waves.

Figure 6:
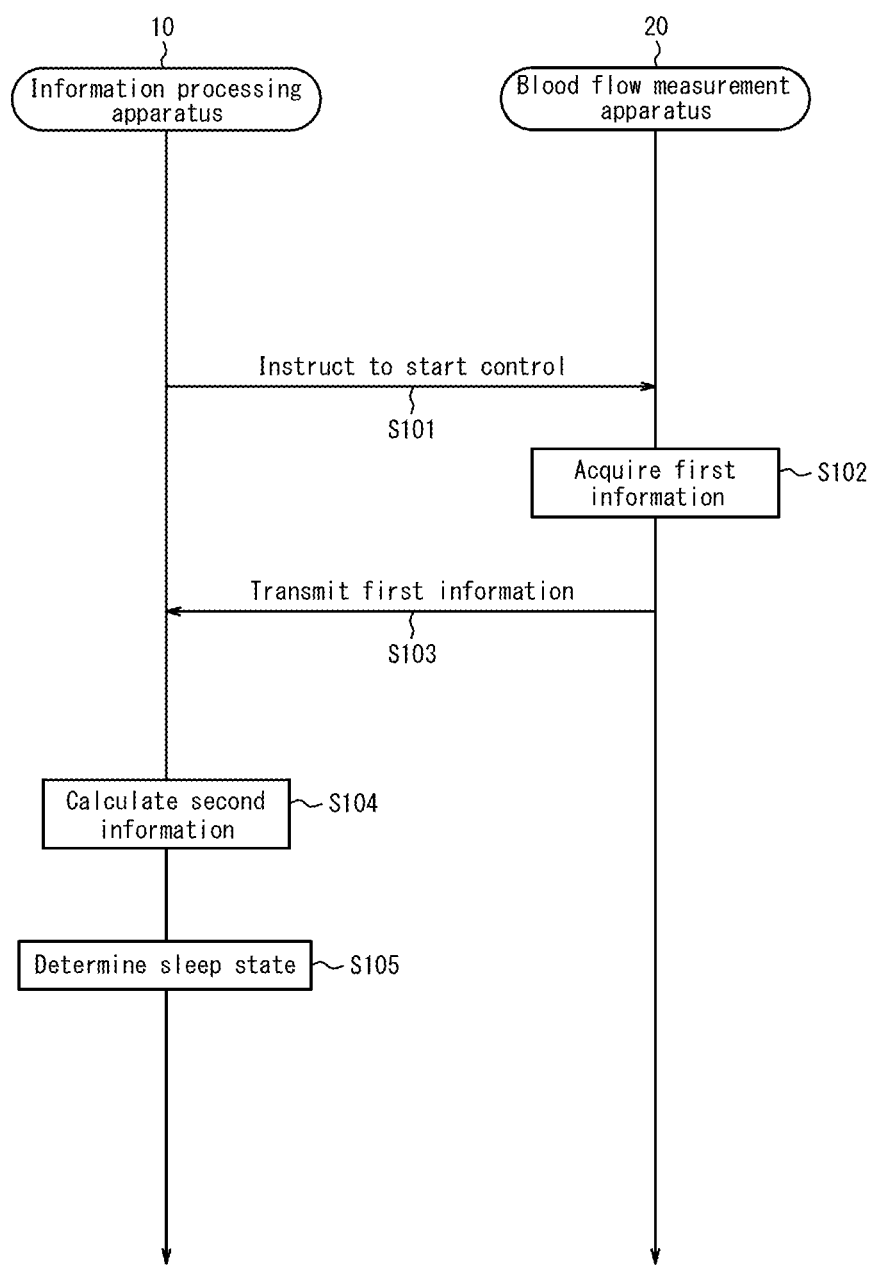
FIG. 6 is a sequence diagram illustrating an example of a control procedure at the time of sleep assessment by the sleep assessment system 1 of FIG. 1.

FIG. 6 is a sequence diagram illustrating an example of a control procedure at the time of sleep assessment by the sleep assessment system 1 of FIG. 1. The sequence of FIG. 6 may, for example, be started when the user wears the blood flow measurement apparatus 20 and provides operation input to start control on the information processing apparatus 10.

The information processing apparatus 10 transmits a signal instructing to start control to the blood flow measurement apparatus 20 based on operation input from the user (step S101). The blood flow measurement apparatus 20 receives the signal instructing to start control from the information processing apparatus 10, starts measurement, and acquires the first information (step S102). The blood flow measurement apparatus 20 transmits the acquired first information to the information processing apparatus 10 (step S103). The information processing apparatus 10 calculates the second information based on the first information received from the blood flow measurement apparatus 20 (step S104). The information processing apparatus 10 determines the sleep state based on the second information (step S105).

The sleep assessment system 1 of the present embodiment may be a system for supporting wakefulness based on the user's sleep stage. In this case, the sleep assessment system 1 may include a notification interface 16 and a speaker 126 as illustrated in FIG. 2.

The information processing apparatus 10 includes the notification interface 16. The notification interface 16 can provide notification encouraging wakefulness when the user is to be awakened. The notification may, for example, be sound, vibration, light, an image, or any combination thereof.

The blood flow measurement apparatus 20 includes the speaker 126. The information processing apparatus 10 may transmit a signal causing the blood flow measurement apparatus 20 to provide notification encouraging wakefulness. In this case, the sleep assessment system 1 may notify the user of the timing of awakening by outputting an alarm sound or the like from the speaker 126 of the blood flow measurement apparatus 20.

Specifically, the sleep assessment system 1 executes processing to support wakefulness of the user after the information processing apparatus 10 determines that the user has fallen asleep. The sleep assessment system 1 then uses the notification interface 16 and/or speaker 126 to provide notification to awaken the user at a predetermined appropriate timing. The appropriate timing may be a suitable timing for awakening from a power nap. A power nap refers to short sleep, of approximately 15 to 30 minutes, from which one awakens before entering deep sleep. Deep sleep is, for example, non-REM sleep.

During REM sleep immediately after the user falls asleep (in the state indicated by section A of FIG. 5), for example, sleep is not deep, and the user's fatigue is not relieved. Therefore, if the user is awakened during REM sleep immediately after sleep onset, the user is unlikely to reap the benefits of a power nap, such as improved work efficiency, after awakening.

If the user is in non-REM sleep and δ waves are included in the brain waves (the state indicated by section C of FIG. 5, i.e. the states NREM2, NREM3, NREM4), the user's sleep deepens, making it hard to awaken the user. Furthermore, if the user is awakened while brain waves are in the δ wave state, then the user enters a state called sleep inertia, and brain activity immediately after awakening tends to grow worse. In this case as well, the user is unlikely to reap the benefits of a power nap, such as improved work efficiency.

By contrast, when the user is in a state immediately after entering non-REM sleep, with a high frequency of θ brain waves (the state indicated by section B of FIG. 5, i.e. NREM1), then fatigue is relieved, and sleep inertia after awakening is unlikely. The effects of the power nap are therefore more easily obtained. The predetermined suitable timing may be immediately after the user enters non-REM sleep, while the frequency of θ brain waves is high. Accordingly, the sleep assessment system 1 may awaken the user during the NREM1 sleep state.

Figure 7:
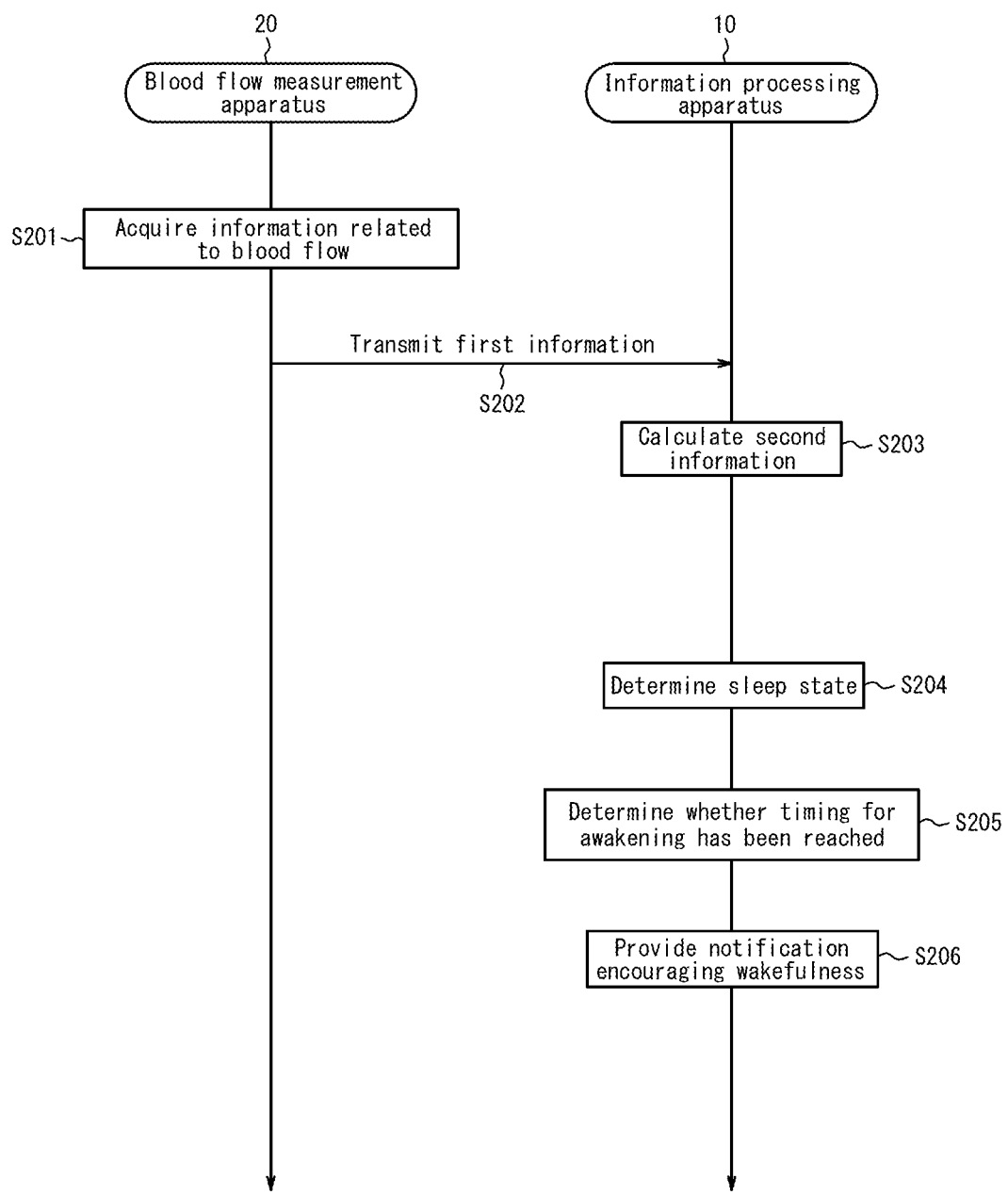
FIG. 7 is a sequence diagram illustrating an example of a control procedure at the time of wakefulness support by the sleep assessment system 1 of FIG. 1.

FIG. 7 is a sequence diagram illustrating an example of a control procedure at the time of wakefulness support by the sleep assessment system 1 of FIG. 1.

The blood flow measurement apparatus 20 acquires the first information (step S201). In other words, the blood flow measurement apparatus 20 acquires the first information at the blood flow measurement unit 24. The blood flow measurement apparatus 20 transmits the acquired first information to the information processing apparatus 10 (step S202). The information processing apparatus 10 calculates the second information based on the first information acquired from the blood flow measurement apparatus 20 (step S203). The information processing apparatus 10 determines the sleep state of the user based on the second information (step S204).

The information processing apparatus 10 furthermore determines whether the timing for awakening the user has been reached based on the sleep state (step S205). The information processing apparatus 10 provides notification encouraging wakefulness via the notification interface 16 when determining that the timing for awakening has been reached (step S206). In step S205, the information processing apparatus 10 may transmit a signal causing the blood flow measurement apparatus 20 to provide notification encouraging wakefulness.

Figure 8:
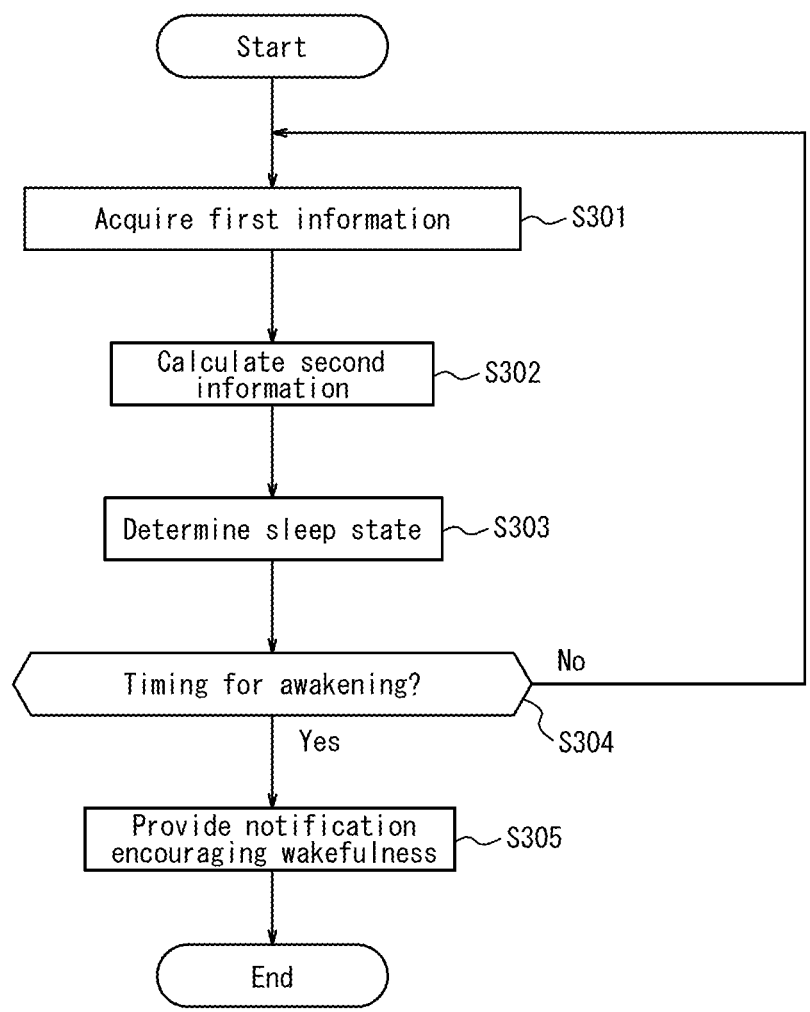
FIG. 8 is a flowchart illustrating the example of the control procedure by an information processing apparatus 10 of FIG. 7 in greater detail.

FIG. 8 is a flowchart illustrating an example of processing executed by the information processing apparatus 10 during the control for wakefulness support of FIG. 7.

The information processing apparatus 10 acquires the first information from the blood flow measurement apparatus 20 (step S301).

The information processing apparatus 10 calculates the second information based on the acquired first information (step S302). The second information may, for example, be the blood flow rate and/or the heartbeat interval.

The information processing apparatus 10 determines the sleep state based on the calculated second information (step S304).

The information processing apparatus 10 furthermore determines whether the timing for awakening the user has been reached based on the determined sleep state (step S305). The information processing apparatus 10 may determine that the timing for awakening has been reached when the user is in a state immediately after entering non-REM sleep, with a high frequency of θ brain waves (the state indicated by section B of FIG. 5, i.e. NREM1).

When determining that the timing for awakening the user has not been reached (step S305: No), the information processing apparatus 10 transitions to step S301 and repeats steps S301 to S305.

When determining that the timing for awakening has been reached (step S305: Yes), the information processing apparatus 10 provides notification encouraging wakefulness via the notification interface 16 (step S306). In step S305, the information processing apparatus 10 may transmit a signal causing the blood flow measurement apparatus 20 to provide notification encouraging wakefulness.

The information processing apparatus 10 has been described as determining the sleep state of the user based on the second information. The information processing apparatus 10 may, however, determine the sleep state based on a different index that can be calculated from the first information and that correlates with the sleep state.

The sleep assessment system 1 of the present embodiment may cause music to be outputted from the speaker 126 of the blood flow measurement apparatus 20. In this case, the sleep assessment system 1 may change the output of music based on the sleep state of the user. For example, as the user's sleep progresses from a light stage to a deep stage, such as from REM sleep to NREM1, NREM2, NREM3, NREM4 in this order, the tempo of the outputted music may be slowed down, and/or the volume may be gradually decreased. Conversely, as the user's sleep progresses from a deep stage to a light stage, the tempo of the outputted music may be sped up, and/or the volume may be gradually increased. The output of music may also be suspended from when the user falls asleep until the timing of awakening.

Figure 9:
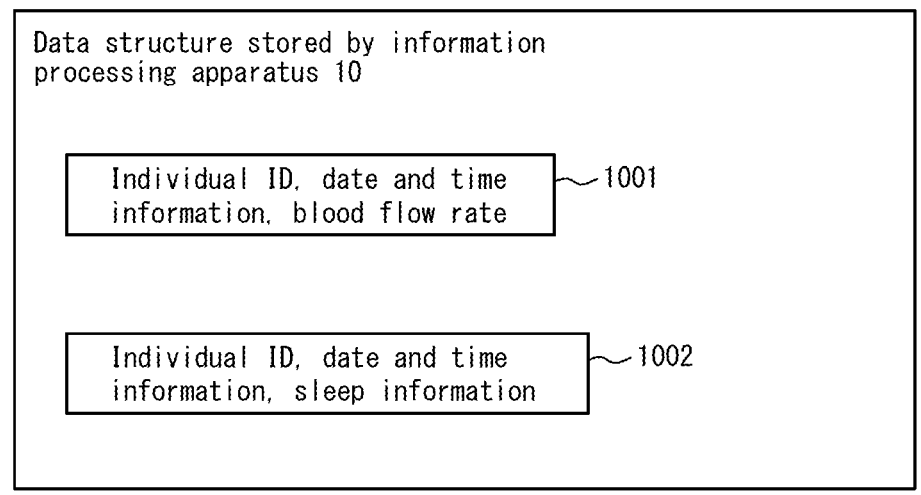
FIG. 9 is a conceptual diagram of the data structure of data stored in a storage 12 of the information processing apparatus 10 of FIG. 2.

Next, the data structure of data stored in the storage 12 of the information processing apparatus 10 is described with reference to FIG. 9. FIG. 9 is a conceptual diagram of the data structure of data stored in the storage 12 of the information processing apparatus 10 illustrated in FIG. 2.

As illustrated in FIG. 9, the information processing apparatus 10 includes blood flow rate data 1001 that includes an individual ID, date and time information, and blood flow rate. The individual ID is information for identifying the user. The date and time information is the date and time of blood flow measurement, the date and time at which the sleep state was determined, or the like and may be a predetermined time point or a predetermined time range. The blood flow rate is information of the blood flow rate measured for the user of the individual ID at the date and time indicated in the date and time information. The information on the blood flow rate includes information such as the change over time in blood flow rate, the heartbeat interval calculated from the blood flow rate, and the like.

As illustrated in FIG. 9, the information processing apparatus 10 includes sleep data 1002 that includes an individual ID, date and time information, and sleep information. The individual ID and the date and time information may be similar to those of the blood flow rate data 1001. The sleep information is information on sleep by the user of the individual ID at the date and time indicated in the date and time information. This sleep information includes information on the assessment of whether the user is sleeping and the assessment of the sleep stage by the assessment unit 17, the length and quality of sleep, the amount of time slept, the time of awakening, and the like. REM sleep, NREM1, NREM2, NREM3, or NREM4 of FIG. 5, for example, may be included in the sleep stage.

In the case of a method for encouraging wakefulness with a timer, for example, during a power nap, notification encouraging wakefulness is provided at the set time regardless of the user's sleep stage. Notification with this method may therefore be provided during REM sleep or when δ waves are dominant. Consequently, the user is unlikely to reap the benefits of a power nap, such as improved work efficiency, after awakening. The suitable timing for awakening also varies by user and varies from day to day. By contrast, the sleep assessment system 1 can determine the suitable timing for awakening based on the aforementioned data structure. The sleep assessment system 1 can thereby determine different suitable timings based on conditions and provide notification at a suitable timing, making it easier for the user to reap the benefits of a power nap.

Other Embodiments

Figure 10:
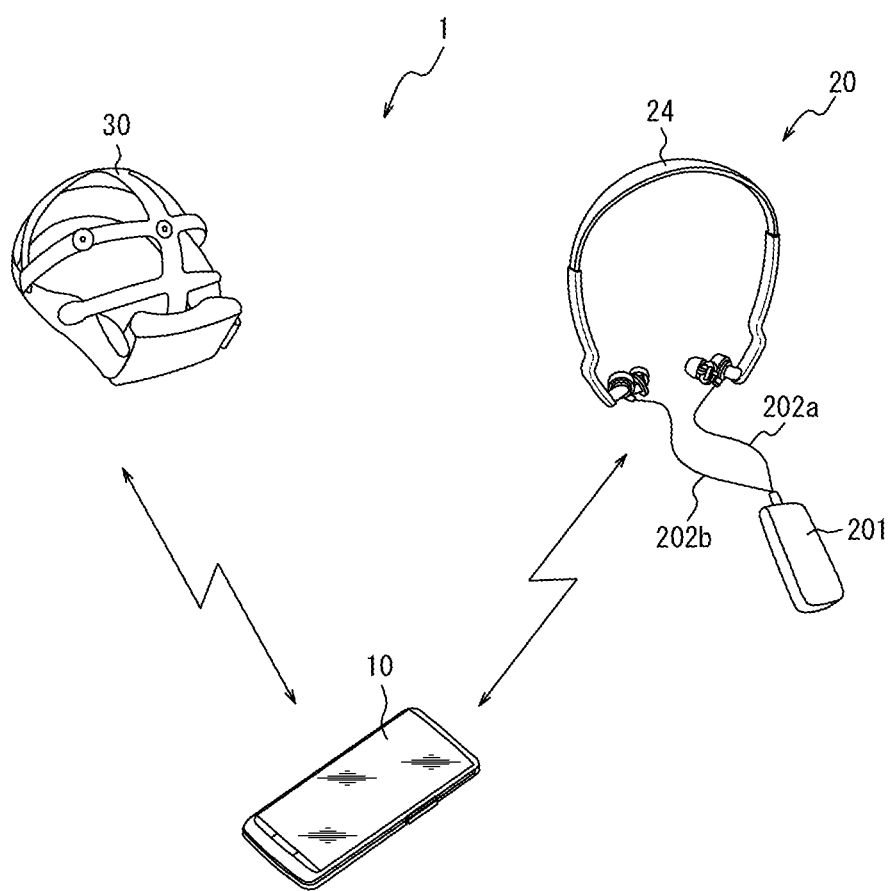
FIG. 10 illustrates the configuration of another embodiment of a sleep assessment system 1 according to the present disclosure.
Figure 11:
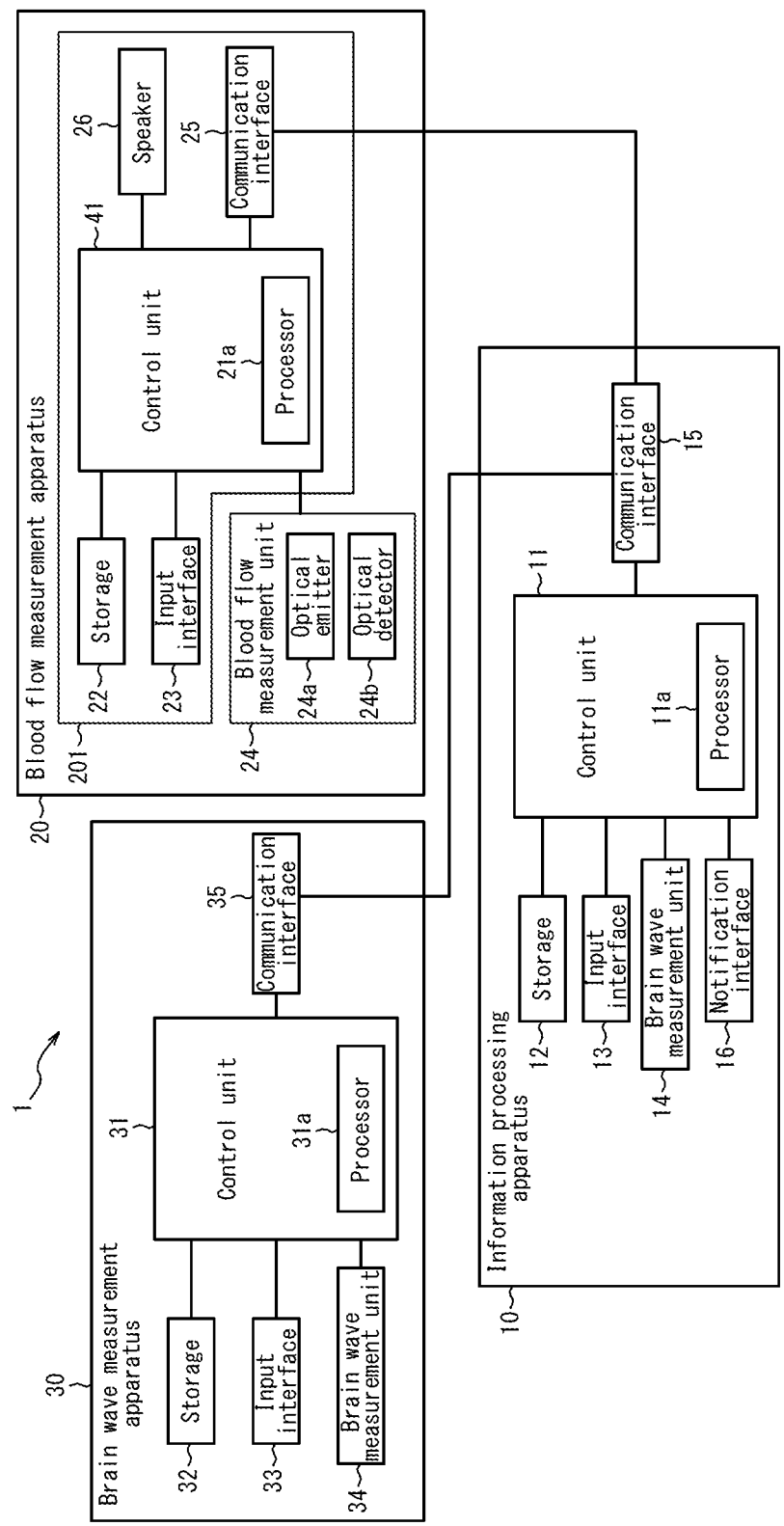
FIG. 11 is a functional block diagram illustrating the schematic configuration of the sleep assessment system 1 of FIG. 10.

FIG. 10 schematically illustrates another embodiment of a sleep assessment system 1 that differs from the above embodiment. FIG. 11 is a functional block diagram illustrating the schematic configuration of the sleep assessment system 1 of FIG. 10.

In the present embodiment, the sleep assessment system 1 may include a brain wave measurement apparatus 30 for measuring brain waves. Consequently, the sleep assessment system 1 can, for example, acquire and store the brain waves of the user at the start of use of the sleep assessment system 1 and can improve the accuracy of sleep assessment using the blood flow measurement apparatus 20.

The brain wave measurement apparatus 30 can acquire third information (second biological information) that is information related to brain waves. The information related to brain waves becomes biological information used for various control in the information processing apparatus 10. The information related to brain waves may, for example, be data of an electric signal, optical signal, or the like that varies based on brain activity. The third information becomes biological information used to perform various control in the information processing apparatus 10. In addition to the second information, the information processing apparatus 10 can calculate fourth information based on the third information.

The fourth information is data yielded by performing calculations on the third information. The fourth information is a brain wave or brain wave signal. This information is a recording of electrical activity by nerve cells in the brain. The brain wave signal is a representation of a brain wave as an electric signal or an optical signal.

The brain wave measurement apparatus 30 may, for example, be configured by a well-known electroencephalograph. The brain wave measurement apparatus 30 is used while worn on the user's head, for example. The brain wave measurement apparatus 30 may, for example, have a frame with a shape wearable on the user's head. As illustrated in FIG. 11, the brain wave measurement apparatus 30 includes a control unit 31, a storage 32, an input interface 33, a brain wave measurement unit 34, and a communication interface 35.

The control unit 31 executes processing to measure the third information of the user. The control unit 31 includes at least one processor 31a that controls and manages the brain wave measurement apparatus 30 overall, starting with the functional blocks of the brain wave measurement apparatus 30. The examples listed in the description of the control unit 11 and the processor 11a of the information processing apparatus 10 may be used as the specific configuration of the control unit 31 and the processor 31a.

The storage 32 stores various information and/or programs for operating the brain wave measurement apparatus 30. The storage 32 can be configured by a semiconductor memory, a magnetic memory, or the like. The storage 32 may also function as a working memory.

The input interface 33 can receive input from the user. The input interface 33 may, for example, be an operation button or a touch panel. The input interface 33 may, for example, be an operation button that controls the power of the brain wave measurement apparatus 30 to be on or off.

The brain wave measurement unit 34 can measure the third information of the user. The brain wave measurement unit 34 may, for example, include a plurality of electrodes. The plurality of electrodes of the brain wave measurement unit 34 may be attached to the frame of the brain wave measurement apparatus 30. The brain wave measurement unit 34 can acquire the third information (for example, a brain wave signal) by inclusion of at least one electrode.

The communication interface 35 can transmit and receive various information to and from each apparatus forming part of the sleep assessment system 1 and/or the outside. Consequently, the communication interface 35 can transmit the third information to the information processing apparatus 10 via the communication interface 15. The brain wave measurement apparatus 30 can also receive information from the outside by communicating with the information processing apparatus 10 via the communication interface 15 and the communication interface 25. The specific configuration of the communication interface 35 and its method for transmitting and receiving information may be similar to those of the communication interface 15 of the information processing apparatus.

Figure 12:
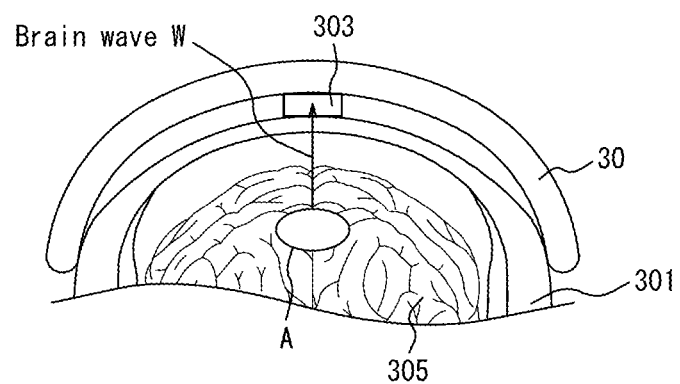
FIG. 12 is a schematic diagram illustrating an example method of wearing a brain wave measurement apparatus 30 of FIG. 10.

The brain wave measurement apparatus 30 is described in greater detail with reference to FIG. 12 and FIG. 13. FIG. 12 is a schematic view of brain wave measurement operations by the brain wave measurement apparatus 30 illustrated in FIG. 10. As illustrated in FIG. 12, the brain wave measurement apparatus 30 includes an electrode 303. Any number, one or greater, of electrodes 303 may be included. The electrode 303 is disposed on a human scalp 301 when the brain wave measurement apparatus 30 is in use. The electrode 303 measures changes in potential over a range A of the brain 305 surface near the electrode 303 as a brain wave W. The number of electrodes 303 in FIG. 12 is one. Any number of electrodes, however, may be used in the present disclosure.

Figure 13:
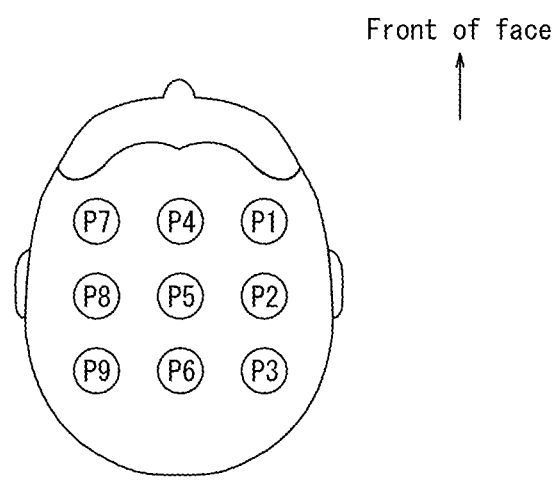
FIG. 13 is a conceptual diagram illustrating an example arrangement of electrodes of the brain wave measurement apparatus 30 of FIG. 10.

FIG. 13 is a conceptual diagram illustrating an example arrangement of electrodes of the brain wave measurement apparatus 30. As illustrated in FIG. 13, a plurality of measurement points are set on a human head, and brain waves are measured by the electrodes as changes in potential. FIG. 13 illustrates nine measurement points, P1 to P9. Any number of measurement points, however, may be included. The positions of the measurement points are not limited to the example illustrated in FIG. 13 and may be any positions. In the present disclosure, the brain wave measurement apparatus 30 measures brain waves at points P1, P2, P3, for example. The measurement points P1 to P9 may be freely combined and designated as brain wave measurement points in the present disclosure.

The information processing apparatus 10 can determine the sleep state based on the third information. In this case, the sleep assessment system 1 can, for example, determine the user's personal sleep state based on the user's own biological information, thereby improving the accuracy of assessment. The blood flow measurement apparatus 20 and the brain wave measurement apparatus 30 can be operated simultaneously to further improve the accuracy of assessment in the sleep assessment system 1.

The third information acquired by the brain wave measurement apparatus 30 may be stored in the storage 12 of the information processing apparatus 10. The information processing apparatus 10 can determine the sleep state based on the third information measured and stored in advance. In this way, the user need not wear the electrode pad of the brain wave measurement apparatus 30 on the head each time the user sleeps. This allows a more convenient assessment of the sleep state.

The brain wave measurement apparatus 30 may be configured integrally with the blood flow measurement apparatus 20. When the brain wave measurement apparatus 30 is configured integrally with the blood flow measurement apparatus 20, it suffices for the user to wear one apparatus configured integrally. This is less hassle than wearing two apparatuses.

Figure 14:
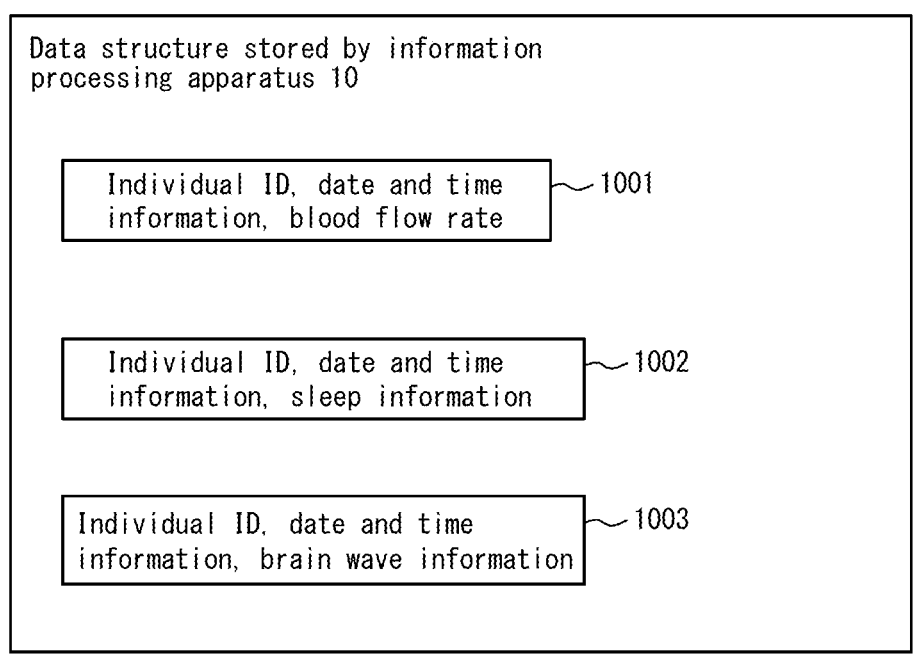
FIG. 14 is a conceptual diagram of the data structure of data stored in a storage 12 of an information processing apparatus 10 of FIG. 10.

FIG. 14 illustrates the data structure of data stored in the storage 12 of the information processing apparatus 10 illustrated in FIG. 10. In this case, the information processing apparatus 10 further includes brain wave data 1003 that includes an individual ID, date and time information, and brain wave information. The brain wave information is information of the brain waves measured for the user of the individual ID at the date and time indicated in the date and time information. The brain wave information includes the type, intensity, change over time, and the like of brain waves.

Figure 15:
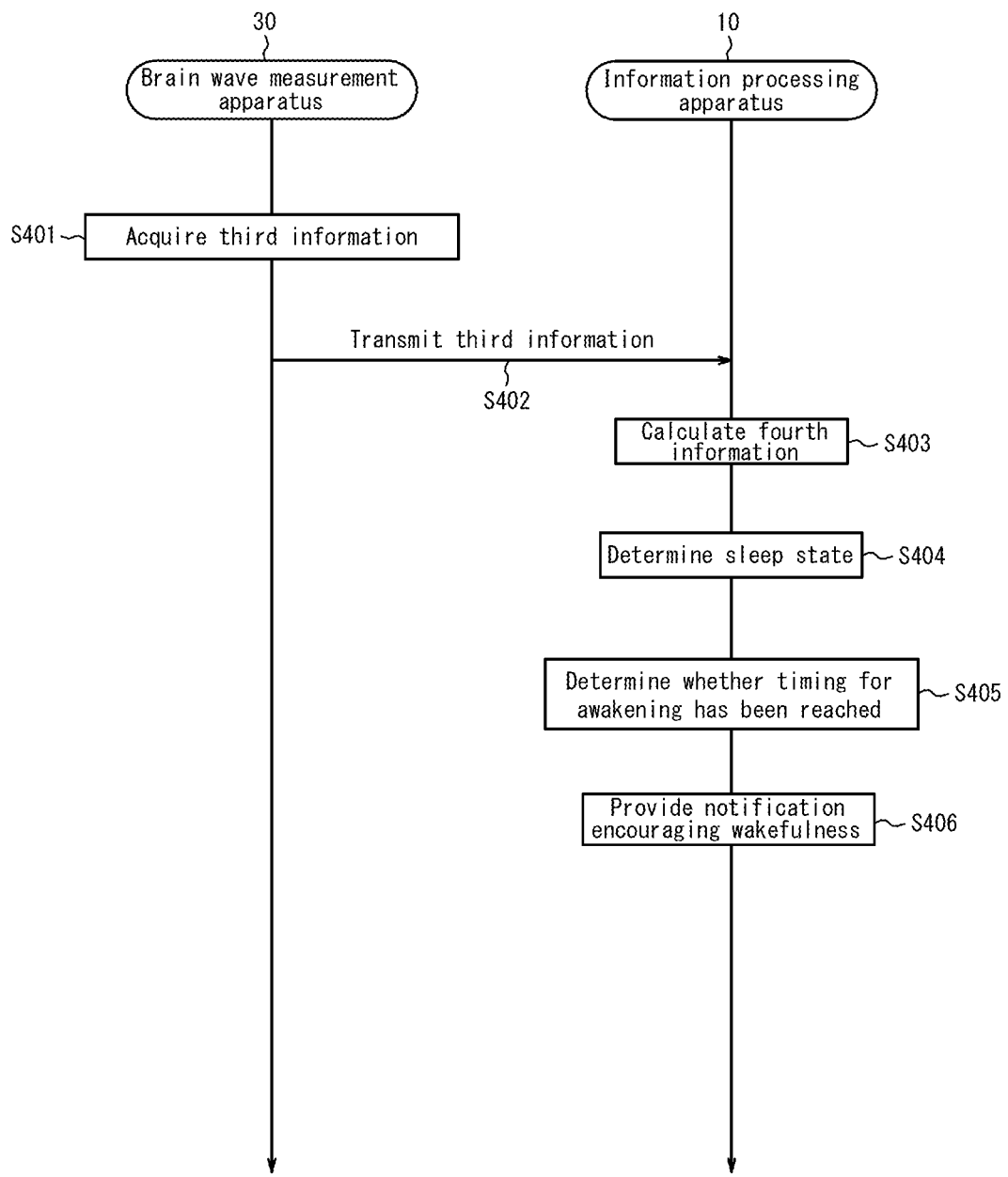
FIG. 15 is a sequence diagram illustrating an example of a control procedure at the time of wakefulness support by the sleep assessment system 1 of FIG. 11.

FIG. 15 is a sequence diagram illustrating an example of a control procedure for wakefulness support by the sleep assessment system 1 illustrated in FIG. 11.

The brain wave measurement apparatus 30 acquires the third information (step S401). In other words, the brain wave measurement apparatus 30 acquires the third information at the brain wave measurement unit 34.

The brain wave measurement apparatus 30 transmits the acquired third information to the information processing apparatus 10 (step S402).

The information processing apparatus 10 calculates the fourth information based on the third information acquired from the brain wave measurement apparatus 30 (step S403).

The information processing apparatus 10 determines the sleep state based on the fourth information (step S404). For example, the information processing apparatus 10 determines the ratio of θ waves and/or δ waves included in the brain waves among the fourth information.

The information processing apparatus 10 determines whether the timing for awakening the user, such as the above-described predetermined suitable timing, has been reached based on the sleep state (step S405).

The information processing apparatus 10 provides notification encouraging wakefulness via the notification interface 16 when determining that the timing for awakening has been reached (step S406). The notification encouraging wakefulness may, for example, be sound, vibration, light, an image, or any combination thereof.

Figure 16:
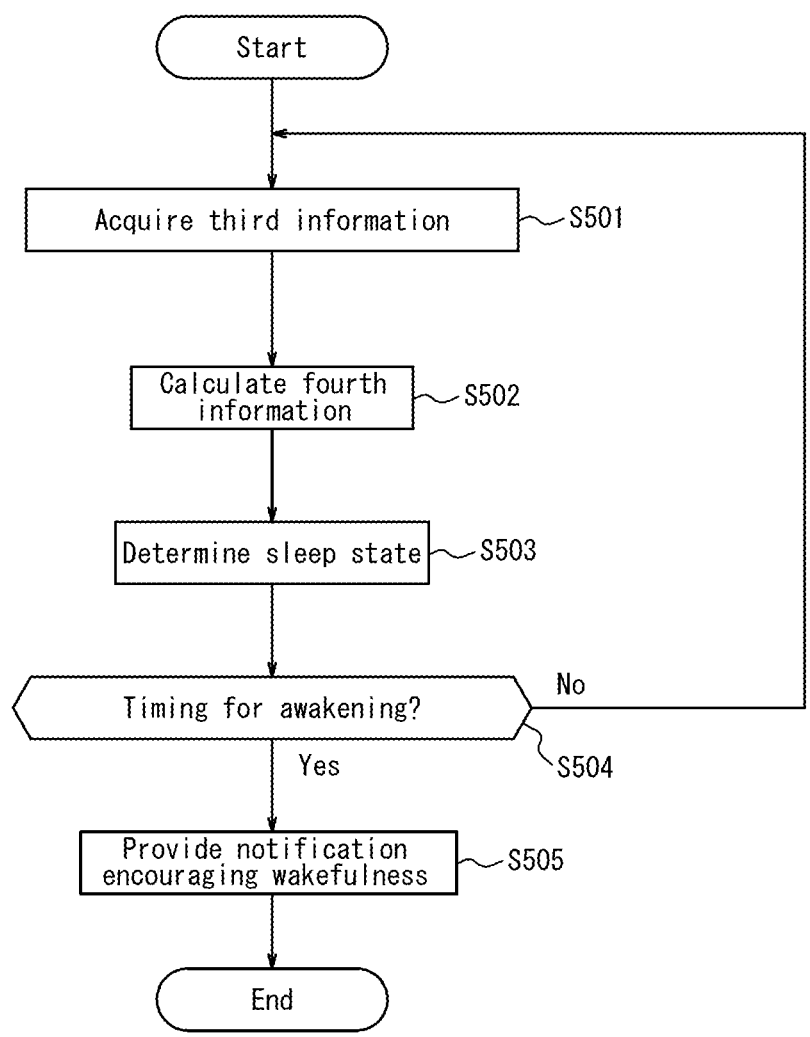
FIG. 16 is a flowchart illustrating the example of the control procedure by the information processing apparatus 10 of FIG. 15 in greater detail.

FIG. 16 is a flowchart illustrating an example of processing executed by the information processing apparatus 10 during the control for wakefulness support of FIG. 15.

The information processing apparatus 10 acquires the third information from the brain wave measurement apparatus 30 (step S501).

The information processing apparatus 10 calculates the fourth information based on the acquired third information (step S502).

The information processing apparatus 10 determines the sleep state based on the fourth information (step S503).

The information processing apparatus 10 furthermore determines whether timing for awakening the user has been reached based on the determined sleep state (step S504). The information processing apparatus 10 may determine that the timing for awakening has been reached when the user is in a state immediately after entering non-REM sleep, with a high frequency of θ brain waves (the state indicated by section B of FIG. 5, i.e. NREM1).

When determining that the timing for awakening the user has not been reached (step S504: No), the information processing apparatus 10 transitions to step S501 and repeats steps S501 to S504.

When determining that the timing for awakening has been reached (step S504: Yes), the information processing apparatus 10 provides notification encouraging wakefulness via the notification interface 16 (step S505).

The present disclosure is not limited to the above embodiments. A variety of changes and improvements may be made without departing from the spirit and scope of the present disclosure.

For example, in the above embodiments, the information acquired or acquired and calculated by the blood flow measurement apparatus 20 is the first information, and the information calculated by the information processing apparatus 10 from the first information is the second information. Also, in the above embodiments, the integral value of the power spectrum has been described as being calculated by the blood flow measurement apparatus 20, and the blood flow rate as being calculated by the information processing apparatus 10. The blood flow measurement apparatus 20 may perform calculations up to and including the blood flow rate, however.

In the above embodiments, the data acquired by the blood flow measurement apparatus 20 through the integral value of the power spectrum has been described as being the first information, but the first information is not limited to this case. For example, the first information may simply be the voltage outputted by a sensor, and the calculation of the power spectrum may be performed within the information processing apparatus 10 as the second information.

In the above embodiments, the blood flow measurement apparatus 20 has been described as including the controller 201, but the controller 201 may be mounted in the information processing apparatus 10. In other words, the blood flow measurement apparatus 20 may be controllable via the information processing apparatus 10.

(Massage System)

Embodiment

The following describes a massage system 2 according to an embodiment of the present disclosure.

Figure 17:
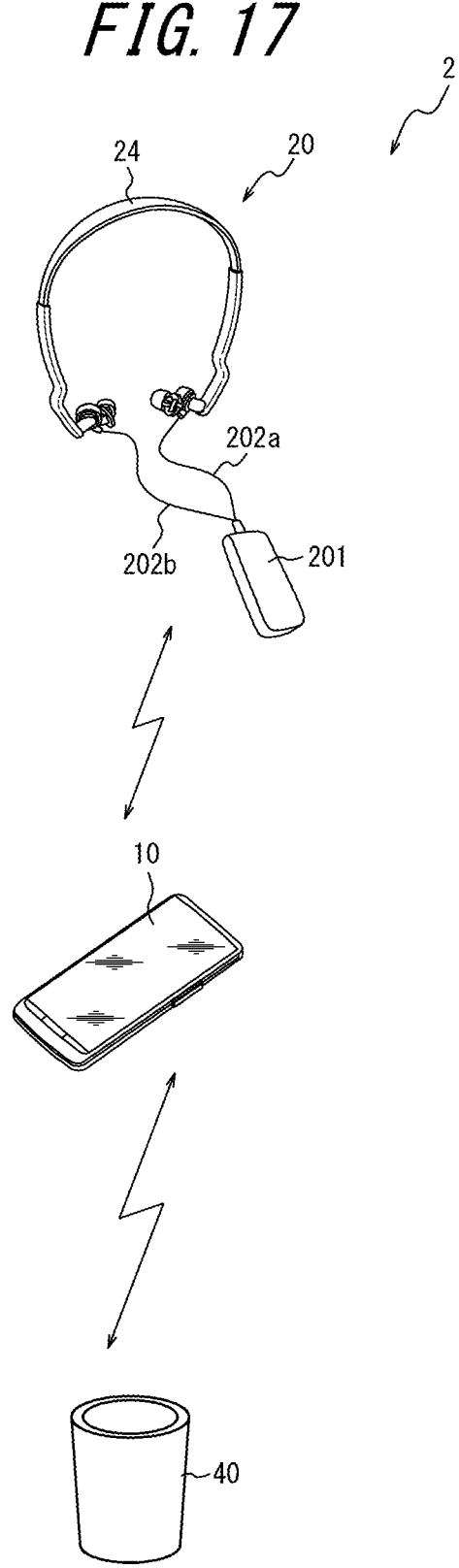
FIG. 17 illustrates the configuration of an embodiment of a massage system 2 according to the present disclosure.
Figure 18:
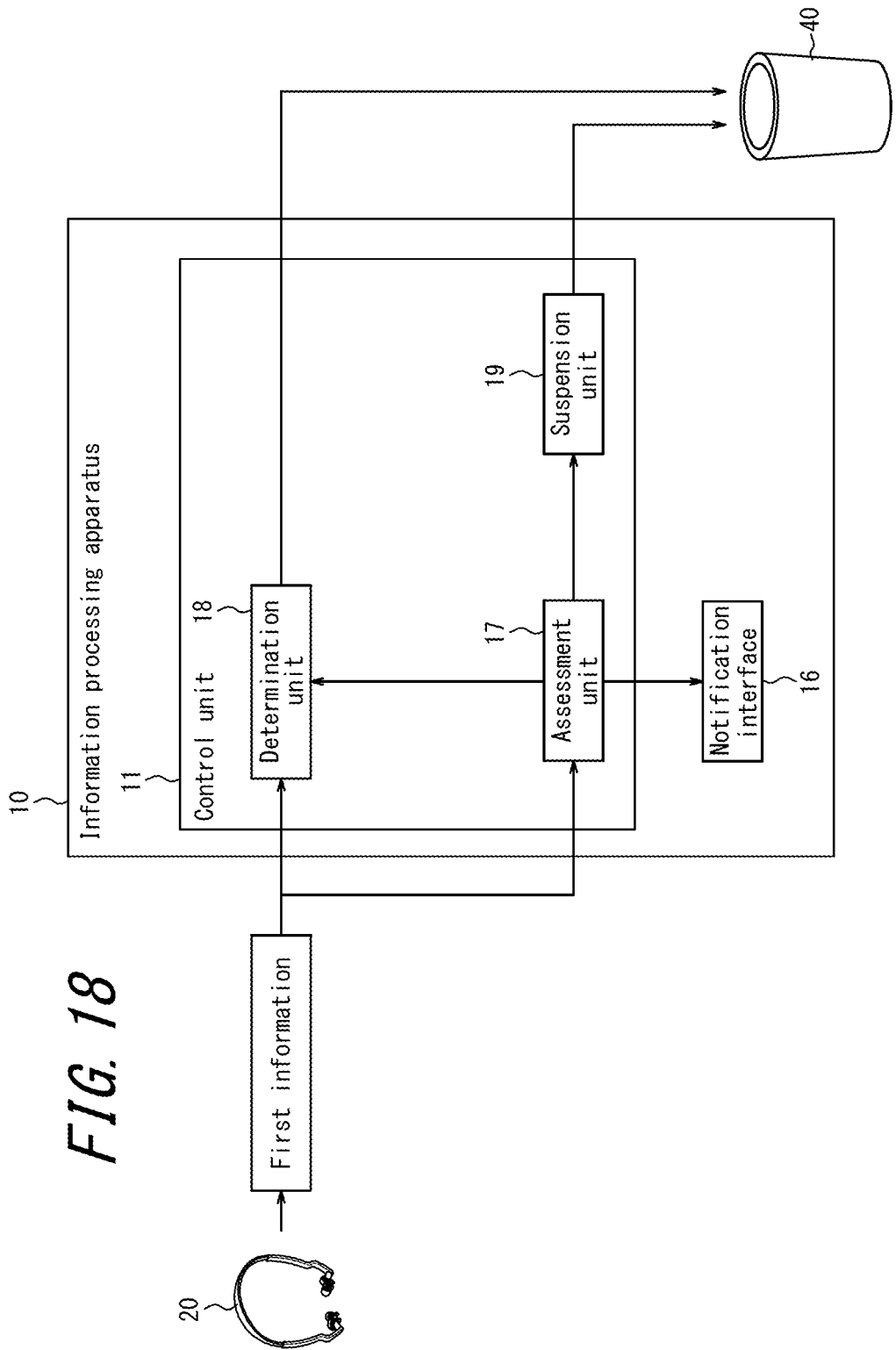
FIG. 18 is a schematic view illustrating the functions of an information processing apparatus 10 of FIG. 17.
Figure 19:
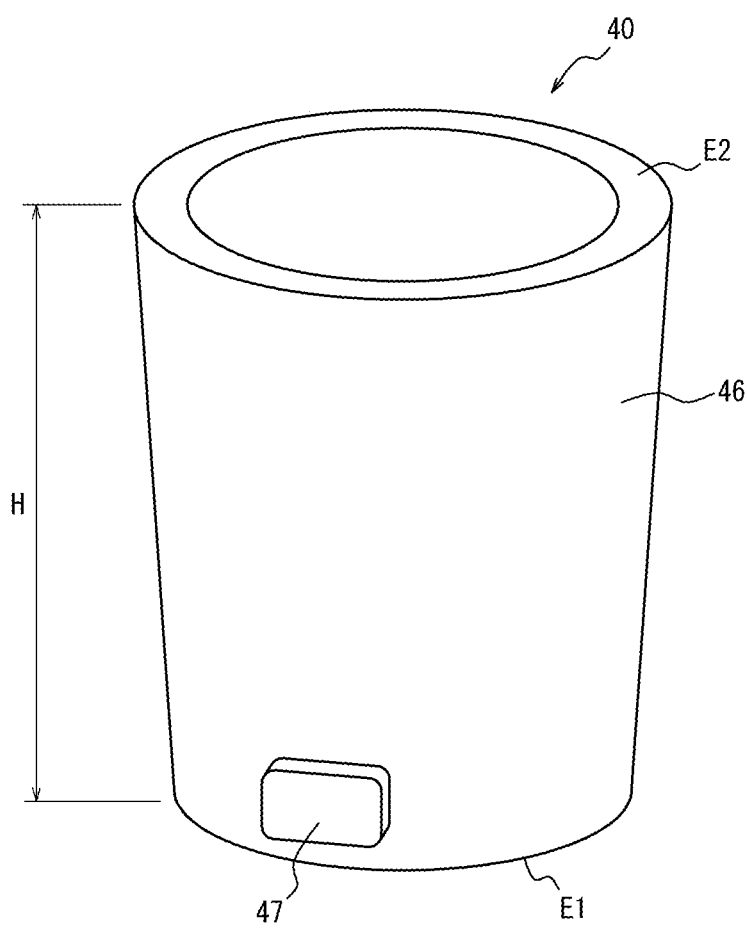
FIG. 19 schematically illustrates the appearance of a massage apparatus 40 of FIG. 17.

FIG. 17 schematically illustrates the configuration of the massage system 2 according to an embodiment. FIG. 18 is a schematic view illustrating the functions of an information processing apparatus 10 of FIG. 17. FIG. 19 is an external perspective view schematically illustrating a massage apparatus 40 of FIG. 17.

The massage system 2 includes the above-described sleep assessment system 1 and massage apparatus 40. Consequently, the massage system 2 can link the sleep assessment system 1 and the massage apparatus 40. In other words, the massage apparatus 40 receives a signal from the information processing apparatus 10 and performs a massage based on the sleep state. For example, the massage apparatus 40 may perform a massage when the user has not fallen asleep.

The massage refers to the massage apparatus 40 applying pressure to a predetermined body part of the user. The predetermined body part may, for example, be the neck, shoulder, waist, foot, hand, or the like, or any combination of thereof. The massage apparatus 40 may, for example, be used individually or in combination with any apparatus such as a massage chair, a foot massager, or the like. In the present embodiment, the massage apparatus 40 is described as being a massage apparatus wearable by the user.

In the present embodiment, the massage refers to the act of rubbing, pressing, pinching, kneading, or hitting a predetermined body part, or to any combination of these actions. The massage includes actions performed using a machine or other object, actions performed by a human, and combinations thereof. The massage deforms the predetermined body part in a predetermined manner.

The massage apparatus 40 of the present embodiment includes a massage apparatus body 46 and a control mechanism 47 disposed in the massage apparatus body 46.

The massage apparatus body 46 in the massage apparatus 40 houses the below-described massage unit 44 and the control mechanism 47 and is worn by the user. The massage apparatus body 46 according to the present embodiment is substantially cylindrical and is configured to be attachable to the user. The user inserts an arm or leg, for example, through the substantially cylindrical massage apparatus body 46 and uses the massage apparatus 40 while the massage apparatus body 46 is worn on the arm or leg.

In the present disclosure, the massage apparatus body 46 is described as being worn on a calf. The massage apparatus body 46 may, however, be worn instead on an arm, thigh, ankle, wrist, head, waist, finger, any other location, or any combination thereof. Instead of being substantially cylindrical, the massage apparatus body 46 may have a polygonal or elliptical shape, any other shape formed by a combination of curves and lines, or any combination of these shapes in the top view described below.

In the present disclosure, the substantially cylindrical shape of the massage apparatus body 46 may include the case of the diameter at the distal end E1 differing from the diameter at the heart-side end E2. The substantially cylindrical shape of the massage apparatus body 46 may, for example, include a shape in which the diameter decreases from the distal end E1 towards the heart-side end E2 and may include the opposite shape. The substantially cylindrical shape of the massage apparatus body 46 may, for example, include a shape such that the diameter changes appropriately based on the position in the height H direction to conform to the shape at the position where the massage apparatus body 46 is worn on the body. In the present disclosure, the view of the massage apparatus body 46 from the heart-side end E2 is referred to as the top view, and from a direction orthogonal to the height H as the side view.

The massage unit 44 may, for example, be covered by a material such as stretchable fiber. Polyester, nylon, cotton, hemp, rubber, another material, or any combination of these may, for example, be used in the massage unit 44. A mixture of these materials at an appropriate ratio may also be used. Configuration of the massage unit 44 with stretchable material allows the massage apparatus 40 to be worn and taken off more easily and makes the massage apparatus 40 less likely to fall off.

While not illustrated, the control mechanism 47 includes a control unit 41, a storage 42, an input interface 43, and a communication interface 45.

The control unit 41 controls and manages the massage apparatus 40. The control unit 41 includes at least one processor 41*a* that controls and manages the massage apparatus 40 overall, starting with the functional blocks of the massage apparatus 40. The functions of the control unit 41 are implemented by the at least one processor 41*a*, which is a CPU or the like that executes a program prescribing control procedures. Such a program may, for example, be stored in the storage 42 or on an external storage medium or the like connected to the massage apparatus 40. The examples listed in the description of the processor 11*a* may be used as the specific configuration of the processor 41*a*.

The control unit 41 drives the massage unit 44 with a predetermined pattern based on a signal received from the information processing apparatus 10. A massage is performed on the user by the driving of the massage unit 44.

The storage 42 can be configured by a semiconductor memory, a magnetic memory, or the like. The storage 42 stores various information and/or programs for operating the massage apparatus 40. The storage 42 may also function as a working memory.

The input interface 43 transmits an input signal based on input from the user to the control unit 41. The input interface 43 accepts operation input from the user of the massage apparatus 40 and may be configured by operation buttons, for example. The input interface 43 may, for example, be an operation button that controls the power of the massage apparatus 40 to be on or off.

The massage unit 44 performs a massage by applying pressure or the like to the user's body. In one embodiment, the massage unit 44 is configured by an actuator that expands and contracts upon application of a voltage. The massage unit 44 is, for example, disposed in the massage apparatus body 46 of the massage apparatus 40.

Figure 20:
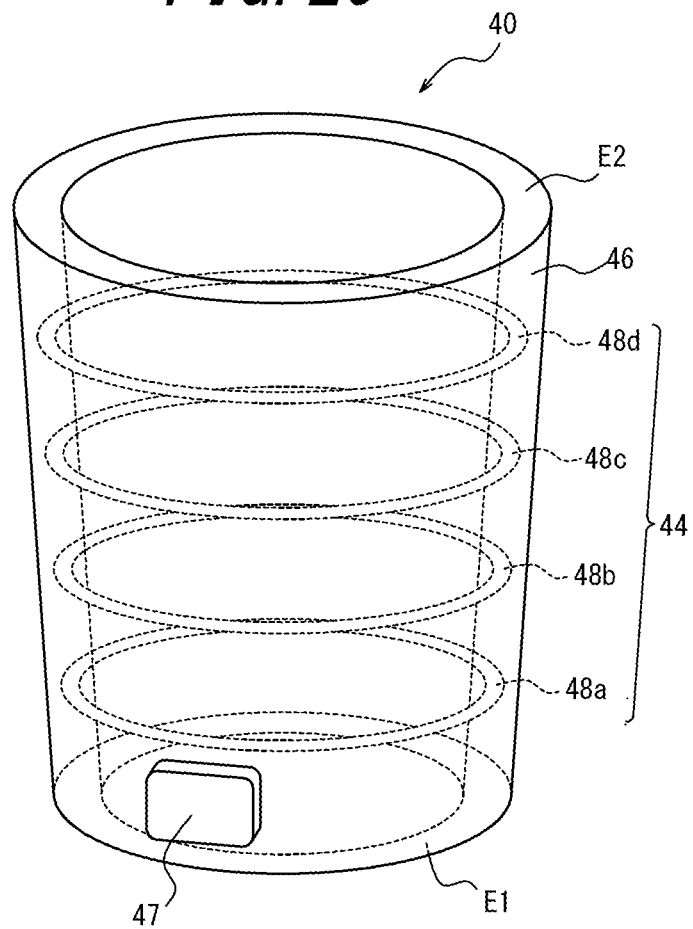
FIG. 20 schematically illustrates the internal configuration of the massage apparatus 40 of FIG. 17.

FIG. 20 schematically illustrates the internal configuration of the massage apparatus 40 illustrated in FIG. 17. As illustrated in FIG. 20, the massage apparatus body 46 includes four actuators 48*a*, 48*b*, 48*c*, 48*d* as the massage unit 44. The four actuators 48*a*, 48*b*, 48*c*, 48*d* are disposed along the circumference of the substantially cylindrical massage apparatus body 46. The four actuators 48*a*, 48*b*, 48*c*, 48*d* may each be linear members. The four actuators 48*a*, 48*b*, 48*c*, 48*d* are disposed in this order from the distal end E1 towards the heart-side end E2. In the present disclosure, the four actuators 48*a*, 48*b*, 48*c*, 48*d* are collectively referred to as the "actuator 48" when no distinction therebetween is made. The actuators 48 are disposed along the circumferential direction in the massage apparatus body 46. In the example illustrated in FIG. 20, the massage apparatus body 46 includes four actuators 48. The number of actuators 48 provided in the massage apparatus body 46, however, is not limited to four. The massage apparatus body 46 may include any number of actuators 48.

In the massage apparatus body 46, the control mechanism 47 and the actuators 48 are arranged at different positions. For example, the control mechanism 47 and the actuators 48 are arranged so as not to overlap in a side view of the massage apparatus body 46. When the control mechanism 47 is disposed between the actuators 48 in the side view (for example, between the actuators 48*a* and 48*b*), the control mechanism 47 may be disposed in the middle (such as the approximate center) of two actuators 48 located on either side of the control mechanism 47.

The actuators 48 expand and contract upon application of a voltage. The expansion and contraction of the actuators 48 presses the body part where the massage apparatus 40 is worn, providing the user with a massage.

The actuators 48 may be configured to include a material known as artificial muscle. The actuators 48 may, for example, be configured to include a conducting high-molecular weight polymer actuator. The high-molecular weight polymer actuator contracts as a result of ion migration within an ion exchange resin due application of a voltage.

Figure 21:
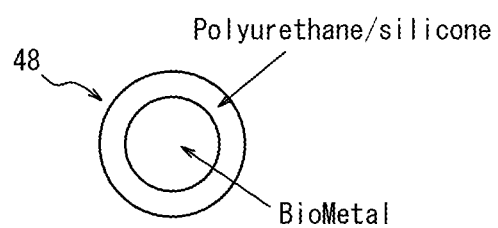
FIG. 21 is a schematic cross-section of an actuator 48 of the massage apparatus 40 of FIG. 17.

FIG. 21 is a schematic cross-section of the actuator 48. The actuator 48 may, for example, be configured to include BioMetal® (BioMetal is a registered trademark in Japan, other countries, or both). When the actuator 48 is configured to include BioMetal as illustrated in FIG. 21, the linear BioMetal is covered by polyurethane and silicone. Upon a voltage being applied to the BioMetal, the surrounding polyurethane and silicone expand and contract, thereby pressing the user.

The communication interface 45 can transmit and receive various information to and from the information processing apparatus 10 and the outside. The specific configuration of the communication interface 45 and its method for transmitting and receiving information may be similar to the communication interface 15.

As illustrated in FIG. 18, the control unit 11 of the information processing apparatus 10 may further include a determination unit 18 that determines the timing for performing a massage and a suspension unit 19 that performs control to suspend the massage. The massage apparatus 40 can perform a massage.

Figure 22:
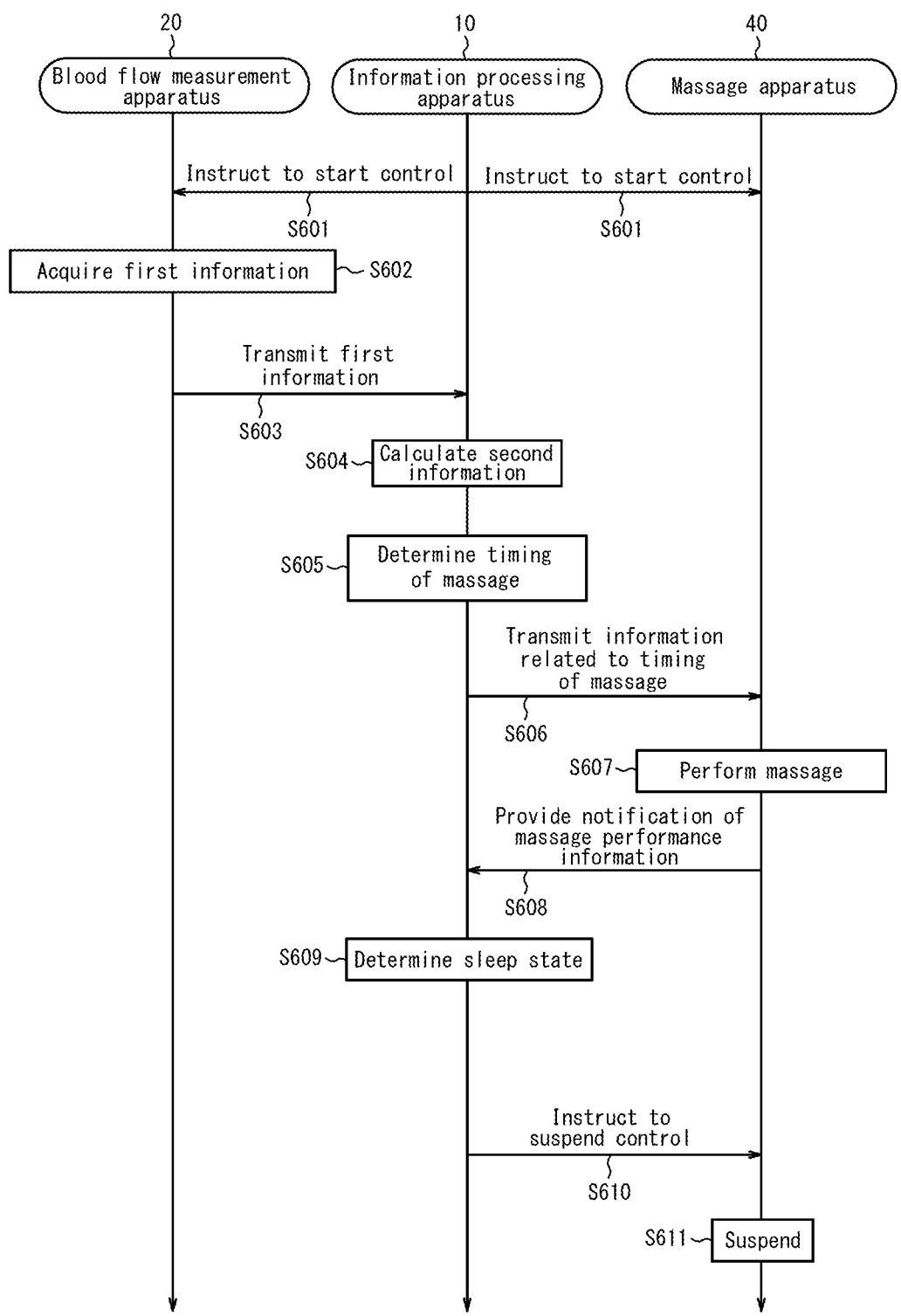
FIG. 22 is a sequence diagram illustrating an example of a control procedure at the time of sleep onset support by the massage system 2 of FIG. 17.

FIG. 22 is a sequence diagram illustrating an example of a control procedure for sleep onset support by the massage system 2. The sequence of FIG. 22 may, for example, be started when the user wears the massage apparatus 40 and the blood flow measurement apparatus 20 and provides operation input to start control on the information processing apparatus 10.

The information processing apparatus 10 transmits a signal instructing to start control to the massage apparatus 40 and the blood flow measurement apparatus 20 based on operation input from the user (step S601). The massage apparatus 40 and the blood flow measurement apparatus 20 each begin operating upon receiving the signal, from the information processing apparatus 10, instructing to start control. The blood flow measurement apparatus 20 acquires the first information of the user (step S602).

The blood flow measurement apparatus 20 transmits the acquired first information to the information processing apparatus 10 (step S603).

The information processing apparatus 10 calculates the second information based on the first information received from the blood flow measurement apparatus 20 (step S604). The information processing apparatus 10 determines the timing of the massage based on the second information (step S605). For example, the information processing apparatus 10 determines the timing of pressure application. Here, an example of the method of determining the timing of a massage by the information processing apparatus 10 is described.

The determination unit 18 of the information processing apparatus 10 may determine the timing of the massage based on the second information calculated by the control unit 11 from the first information. The determination unit 18 may determine the timing of the massage based on the volume pulse wave or the acceleration pulse wave among the second information, for example.

Figure 23A:
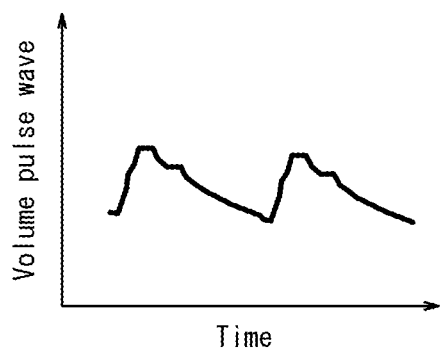
FIG. 23A schematically illustrates an example of a volume pulse wave, and FIG. 23B schematically illustrates an example of an acceleration pulse wave.
Figure 23B:
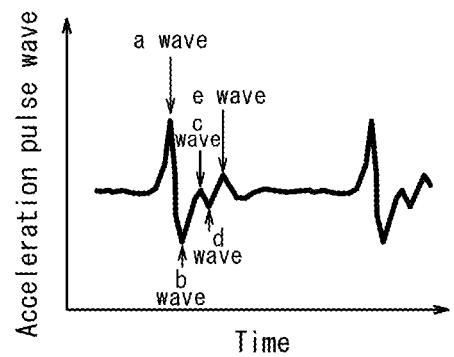

The control unit 11 can calculate the volume pulse wave based on the change over time in the blood flow rate. The control unit 11 can also calculate the acceleration pulse wave by differentiating the blood flow rate twice over time. FIG. 23A schematically illustrates an example of a volume pulse wave. FIG. 23B schematically illustrates an example of an acceleration pulse wave. Based on the blood flow rate, the control unit 21 calculates the volume pulse wave exemplified in FIG. 23A, and based on the volume pulse wave, the control unit 21 calculates the acceleration pulse wave exemplified in FIG. 23B.

As illustrated in FIG. 23B, the acceleration pulse wave includes five component waves called an a wave, b wave, c wave, d wave, and e wave. The a wave is called the early systolic positive wave, and the b wave is called the early systolic negative wave. These waves indicate the early component of systole in the volume pulse wave. The c wave is called the late systolic re-increasing wave, and the d wave is called the late systolic re-decreasing wave. These waves indicate the late component of systole in the volume pulse wave. In other words, the a wave through the d wave are systolic components. By contrast, the e wave is called the early diastolic positive wave and indicates a diastolic component of the volume pulse wave. In other words, the e wave is a diastolic component.

The control unit 11 detects the timing at which the e wave occurs based on the acceleration pulse wave. The control unit 11 may determine the timing of the massage to be the timing at which the e wave occurs. At this time, the information processing apparatus 10 may transmit information related to the timing of the massage while taking into consideration the positional relationship between the body part where the blood flow was measured and the body part where the massage (pressure) is to be performed.

Specifically, in the massage system 2 of the present embodiment, the blood flow at the ear is measured by the blood flow measurement apparatus 20, and a calf is massaged by the massage apparatus 40. Here, the distance from the heart differs between the ear and the calf. Therefore, the timing of the e wave in the acceleration pulse wave of the blood flow differs between the ear and the calf. Based on the timing of the e wave determined from the first information measured at the ear, for example, the information processing apparatus 10 calculates the timing of the e wave at the calf in correspondence with the positional relationship between the ear and the calf. The information processing apparatus 10 may determine the timing of the massage to be the calculated timing at which the e wave occurs at the calf.

The information processing apparatus 10 transmits information related to the determined timing of the massage to the massage apparatus 40 (step S606).

The massage apparatus 40 performs the massage at the timing acquired from the information processing apparatus 10, i.e. at the timing synchronized with the pulse wave (step S607). For example, the massage apparatus 40 performs the massage in synchronization with the timing of the e wave. Specifically, the control unit 41 drives the actuators 48 in conjunction with the timing of the e wave, for example. It becomes easier for the blood flow to be pushed towards the heart accurately, facilitating efficient blood circulation, by the control unit 41 driving the actuators 48 in synchronization with the timing at which the acceleration pulse wave becomes the e wave.

The control unit 41 may drive the four actuators 48a, 48b, 48c, 48d at different timings. For example, the control unit 41 may drive the actuators 48a, 48b, 48c, 48d in this order at the timing of diastole. When the actuators 48 are driven in order from the distal end in this way, the calf is pressed in order from the distal side towards the heart side, making it easier to push blood towards the heart side.

The massage apparatus 40 notifies the information processing apparatus 10 of massage performance information (step S608). The massage performance information includes the start time of the massage, the type and intensity of the massage, and the like.

Step S602 through step S608 may be executed repeatedly. Performance of the massage makes it easier to increase the circulating blood volume that returns to the user's heart. When the circulating blood volume increases, the stroke volume (SV) of blood pumped from the heart to the whole body per heartbeat increases. By Starling's law, the user's brain stimulates the parasympathetic nerves when the SV increases. Stimulation of the parasympathetic nerves makes it easier for the user to relax. Consequently, the user can fall asleep more easily. Execution of steps S602 through S608 by the massage apparatus 40 in this way facilitates induction of sleep onset in the user. In other words, the effects of a massage can be improved by the blood flow measurement apparatus 20 linking the second information of the user with the operations of the massage apparatus 40.

The information processing apparatus 10 can determine the sleep state of the user based on the second information acquired from the blood flow measurement apparatus 20 (step S609). Here, the information processing apparatus 10 determines whether the user has fallen asleep. The information processing apparatus 10 can determine that the user has fallen asleep based on the above-described relationship between brain waves and sleep, such as when α waves become 50% or less and θ waves become dominant.

The information processing apparatus 10 transmits a signal instructing to suspend control to the massage apparatus 40 and the blood flow measurement apparatus 20 when it is determined that the user has fallen asleep (step S610).

The massage apparatus 40 and the blood flow measurement apparatus 20 suspend control upon receiving the signal, from the information processing apparatus 10, for suspending control (step S611).

In response to the signal instructing to suspend control, the massage apparatus 40 and the blood flow measurement apparatus 20 suspend operations when it is determined that the user has fallen asleep. It is therefore unnecessary for the user to provide operation input himself to suspend operations of the massage apparatus 40 and the blood flow measurement apparatus 20. When, for example, a timer is set in advance, the information processing apparatus 10 may suspend operations of the massage apparatus 40 and the blood flow measurement apparatus 20 after the set predetermined time elapses, even if the user has not fallen asleep.

When the user has not fallen asleep, steps S109 through S112 may be repeated.

Figure 24:
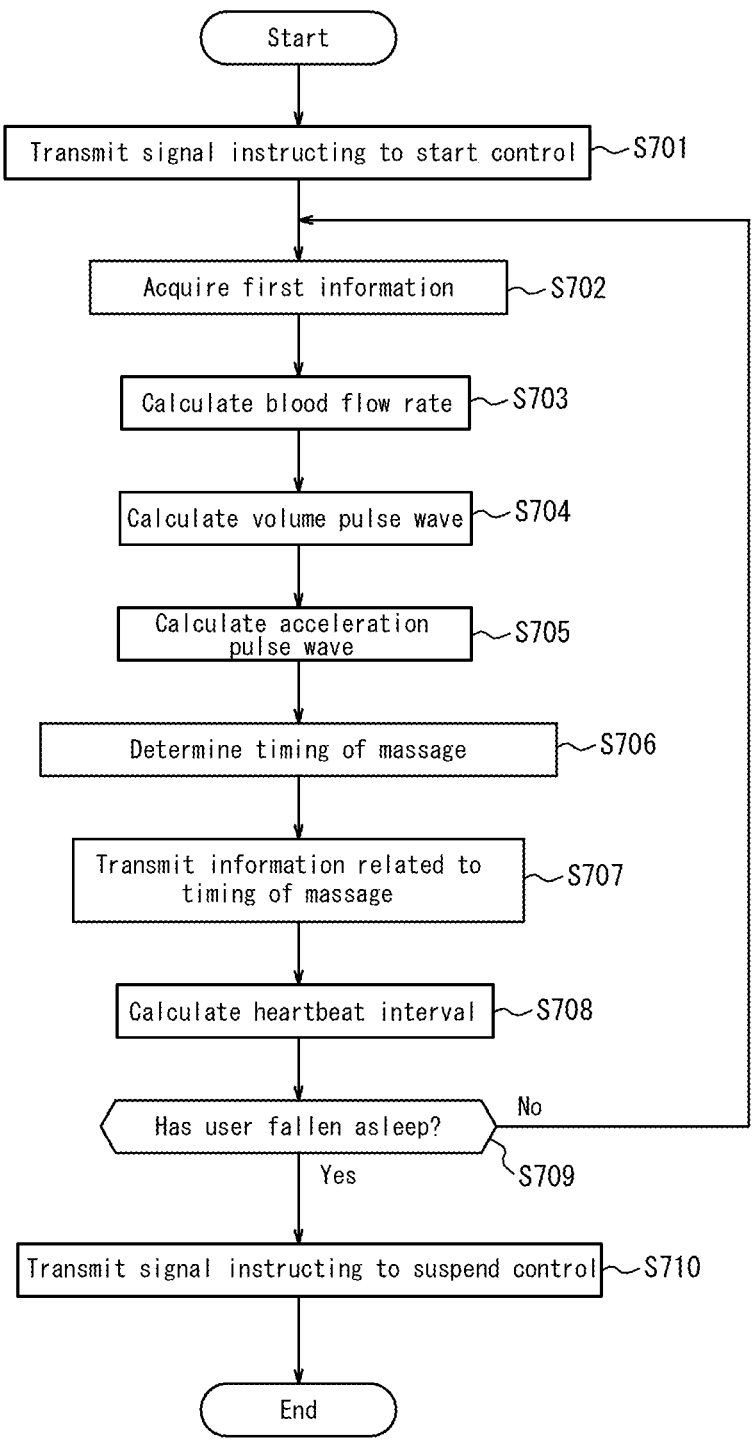
FIG. 24 is a flowchart illustrating the example of the control procedure by the information processing apparatus 10 of FIG. 22 in greater detail.

FIG. 24 is a flowchart illustrating an example of processing executed by the information processing apparatus 10 during the control for sleep onset support of FIG. 22. The flowchart in FIG. 24 specifically illustrates processing executed by the control unit 11.

The information processing apparatus 10 transmits a signal instructing to start control to the massage apparatus 40 and the blood flow measurement apparatus 20 based on operation input from the user (step S701). The massage apparatus 40 and the blood flow measurement apparatus 20 each begin control in response to the signal instructing to start control.

The information processing apparatus 10 acquires the first information from the blood flow measurement apparatus 20 (step S702).

The information processing apparatus 10 calculates the blood flow rate based on the acquired first information (step S703). In this case, the second information is the blood flow rate. The calculation of the blood flow rate can, for example, be made by using the Doppler shift, as described above.

The information processing apparatus 10 calculates the volume pulse wave, an example of which is illustrated in FIG. 16A, based on the calculated blood flow rate (step S704). In other words, the information processing apparatus 10 calculates the volume pulse wave by treating the calculated blood flow rate as being proportional to the change in blood vessel thickness (blood vessel diameter), which becomes the volume pulse wave.

The information processing apparatus 10 calculates the acceleration pulse wave, an example of which is illustrated in FIG. 16B, by differentiating the calculated volume pulse wave twice over time (step S705).

The information processing apparatus 10 determines the timing of the massage based on the acceleration pulse wave (step S706). For example, the information processing apparatus 10 calculates the timing of the e wave in the acceleration pulse wave and determines to perform the massage in synchronization with the timing of the e wave. At this time, the information processing apparatus 10 may determine the timing of the massage taking into consideration the positional relationship between the body part where the blood flow was measured and the body part where the massage is to be performed.

The information processing apparatus 10 transmits information related to the determined timing of the massage to the massage apparatus 40 (step S707). The massage apparatus 40 performs the massage based on the information related to the timing of the massage.

The control unit 11 of the information processing apparatus 10 calculates the heartbeat interval based on the first information (step S708). The assessment unit 17 determines the sleep state of the user (step S709). The suspension unit 19 transmits a signal instructing to suspend control to the massage apparatus 40 when the assessment unit 17 determines that the user has fallen asleep (step S710).

While not illustrated, the information processing apparatus 10 in the massage system 2 includes massage data 1004 in addition to the blood flow rate data 1001 and the sleep data 1002. The massage data 1004 includes an individual ID, date and time information, and massage performance information. The massage performance information is information on a massage performed by the user of the individual ID at the date and time indicated in the date and time information. The massage information includes the type, intensity, duration, and the like of the massage. The individual ID and the date and time information of the massage data 1004 may be similar to those of the blood flow rate data 1001.

Other Embodiment

Figure 25:
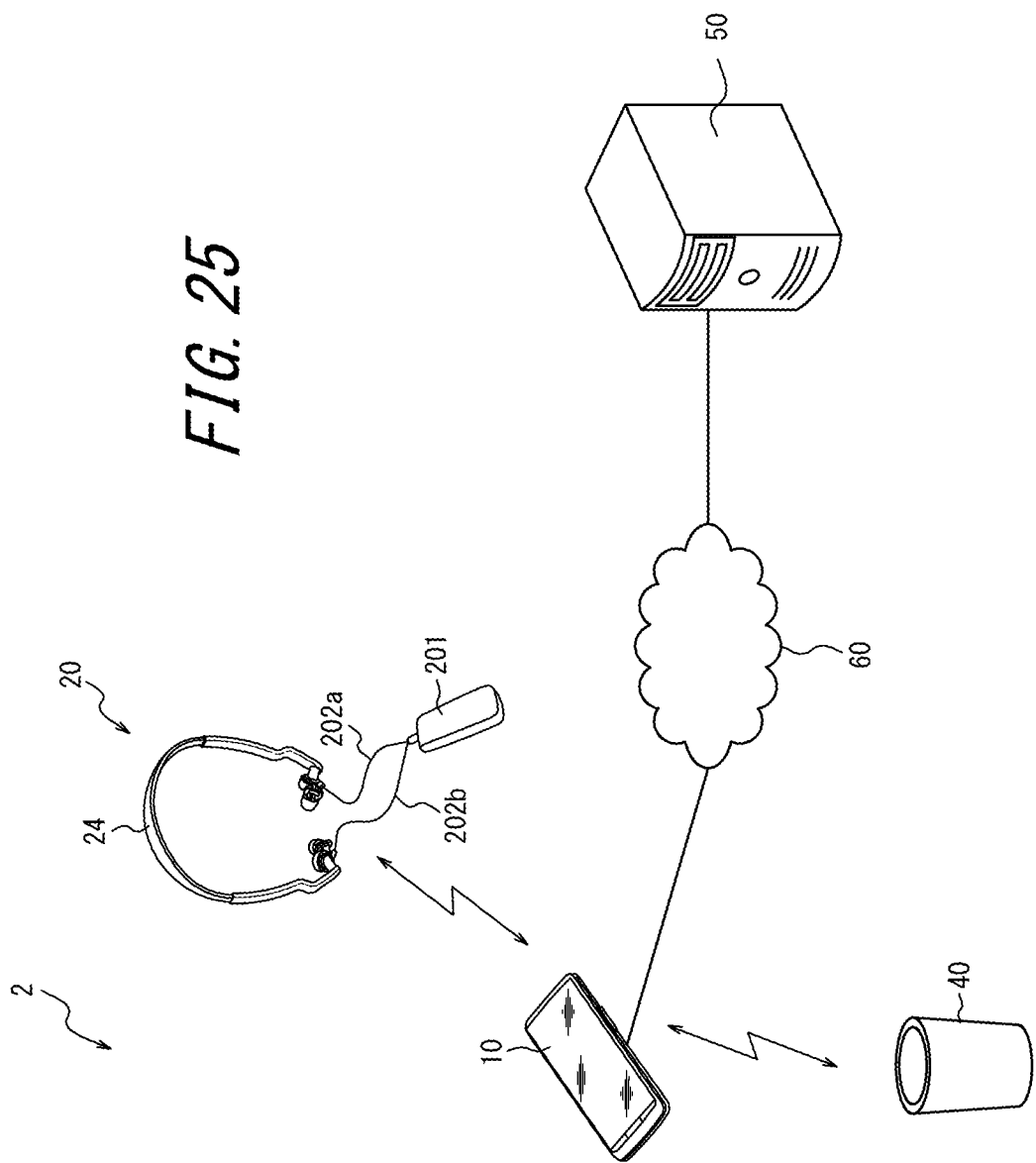
FIG. 25 schematically illustrates the case of the massage system 2 of FIG. 17 being connected to a server 50 over a network 60.

Next, as another embodiment of the massage system 2, the case of the massage system 2 being connected to a server over a network is described. FIG. 25 schematically illustrates the configuration when the massage system 2 is connected to a server 50 over a network 60.

The server 50 is connected to the information processing apparatus 10 over the network 60. The network 60 is wired, wireless, or any combination thereof.

Figure 26:
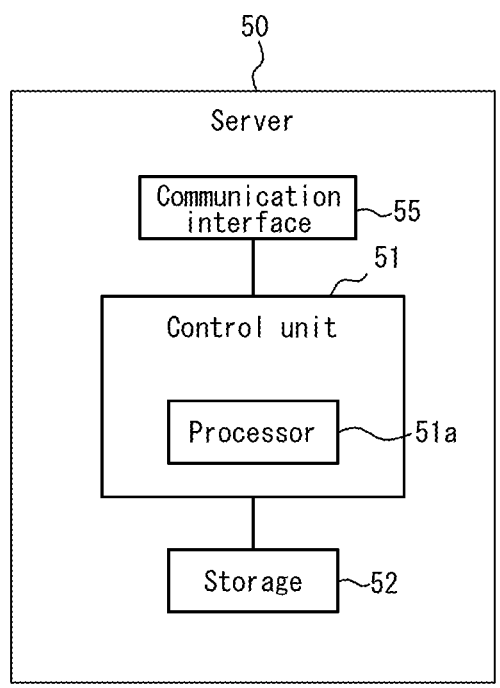
FIG. 26 is a functional block diagram illustrating the schematic configuration of the server 50 of FIG. 25.

Next, with reference to FIG. 26, the internal configuration of the server 50 illustrated in FIG. 25 is described. FIG. 26 is functional block diagram illustrating the schematic configuration of the server 50 illustrated in FIG. 25.

The server 50 includes a communication interface 55, a control unit 51, and a storage 52.

By communicating with the information processing apparatus 10 over the network 60, the communication interface 55 transmits and receives a variety of information. The communication interface 55 can transmit and receive information to and from the information processing apparatus 10 using the network 60, which is wireless, wired, or a combination of wireless and wired. The communication interface 55 can, for example, communicate with Bluetooth®, infrared, NFC, wireless LAN, wired LAN, wide area network (WAN), Internet, any other communication medium, or any combination of these. In an embodiment, the communication interface 55 communicates with the information processing apparatus 10 using the Internet.

The control unit 51 includes at least one processor 51a that controls and manages the server 50 overall, starting with the functional blocks of the server 50. The functions of the control unit 51 are implemented by the at least one processor 51a, which is a CPU or the like that executes a program prescribing control procedures. Such programs may, for example, be stored in the storage 52 or on an external storage medium or the like connected to the server 50. The examples listed in the description of the processor 11a may be used as the specific configuration of the processor 51a.

The storage 52 can be configured by a semiconductor memory, a magnetic memory, or the like. The storage 52 stores various information and/or programs for operating the server 50. The storage 52 may also function as a working memory. For example, the storage 52 may store information acquired by the server 50 from the communication interface 55.

The server 50 receives information from the information processing apparatus 10. The server 50 stores the received information.

Figure 27:
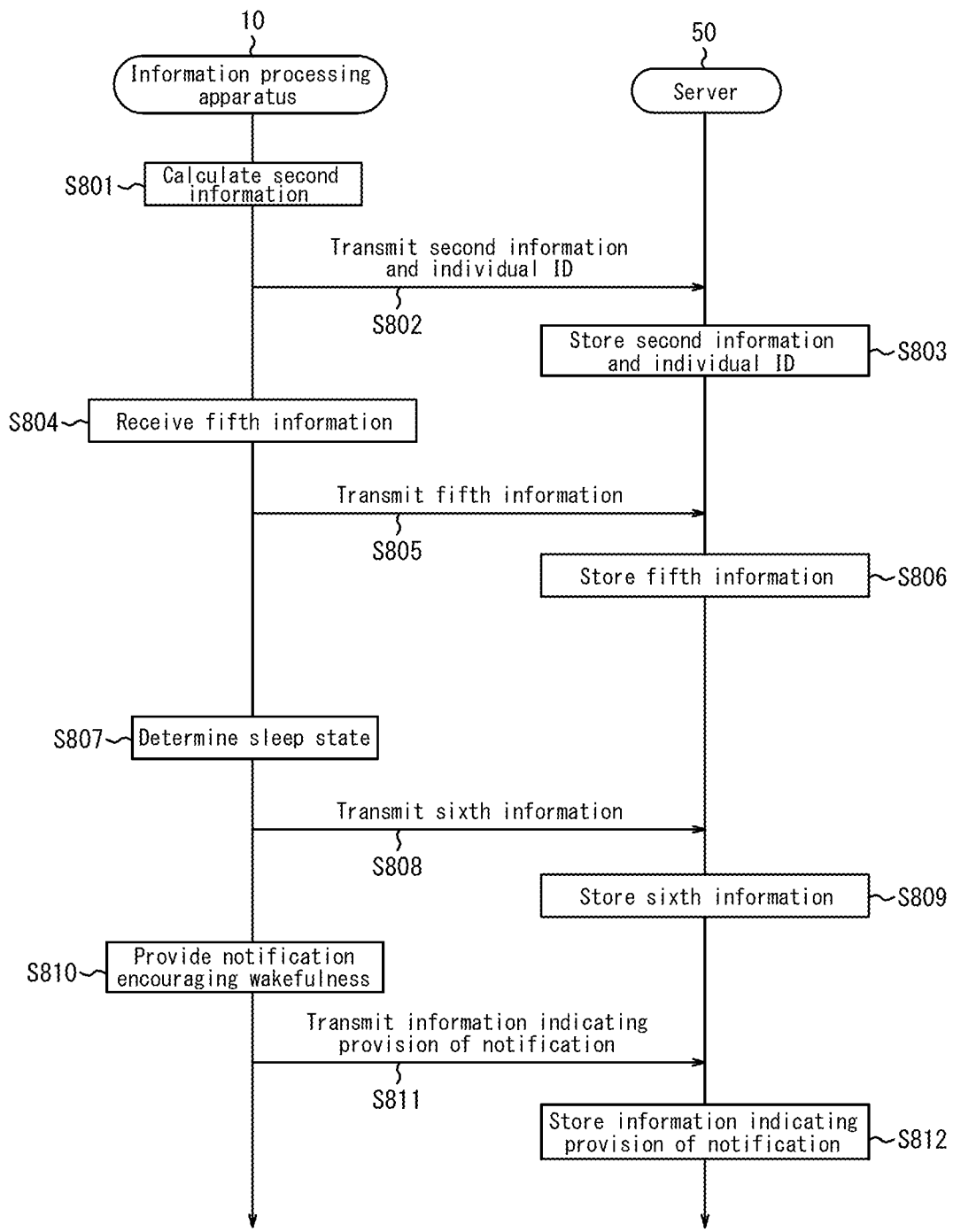
FIG. 27 is a sequence diagram illustrating an example of a control procedure of the massage system 2 of FIG. 25.

Next, with reference to FIG. 27, the operations of the system illustrated in FIG. 25 are described. FIG. 27 is a sequence diagram illustrating an example of a control procedure of the massage system 2 illustrated in FIG. 25.

The information processing apparatus 10 calculates the second information (step S801).

The information processing apparatus 10 transmits the second information and the individual ID to the server 50 (step S802).

The server 50 stores the second information and the individual ID (step S803).

The information processing apparatus 10 receives the massage performance information from the massage apparatus 40 as fifth information (step S804).

The information processing apparatus 10 transmits the fifth information to the server 50 (step S805).

The server 50 stores the fifth information (step S806).

The information processing apparatus 10 determines the sleep state (step S807).

The information processing apparatus 10 transmits the information related to the determined sleep state to the server 50 as sixth information (step S808). The sixth information may, for example, be information indicating the transition of the sleep state from when the user falls asleep until the user wakes up.

The server 50 stores the sixth information (step S809).

The information processing apparatus 10 provides notification encouraging wakefulness (step S810).

The information processing apparatus 10 transmits information indicating provision of notification to the server 50 (step S811).

The server 50 stores the information indicating provision of notification (step S812).

Next, with reference to FIG. 28, the data stored on the server 50 illustrated in FIG. 25 is described. FIG. 28 is a conceptual view of the data stored on the server 50 illustrated in FIG. 25.

As illustrated in FIG. 28, information 10001 containing the second information, the fifth information, and the sixth information, with an individual ID and a date and time as the primary keys, is stored in the storage 52 of the server 50. Information 10002 containing the sex, age, and occupation of the user, with the individual ID of the user as the primary key, is also stored in the storage 52 of the server 50. Information other than the information illustrated in FIG. 28 may be stored on the server 50, or only a portion of the information illustrated in FIG. 28 may be stored on the server 50.

The server 50 can extract sleep conditions by individual, by age, or the like by analyzing the information 10001 and the information 10002 stored in the storage 52.

Other Embodiment

Figure 29:
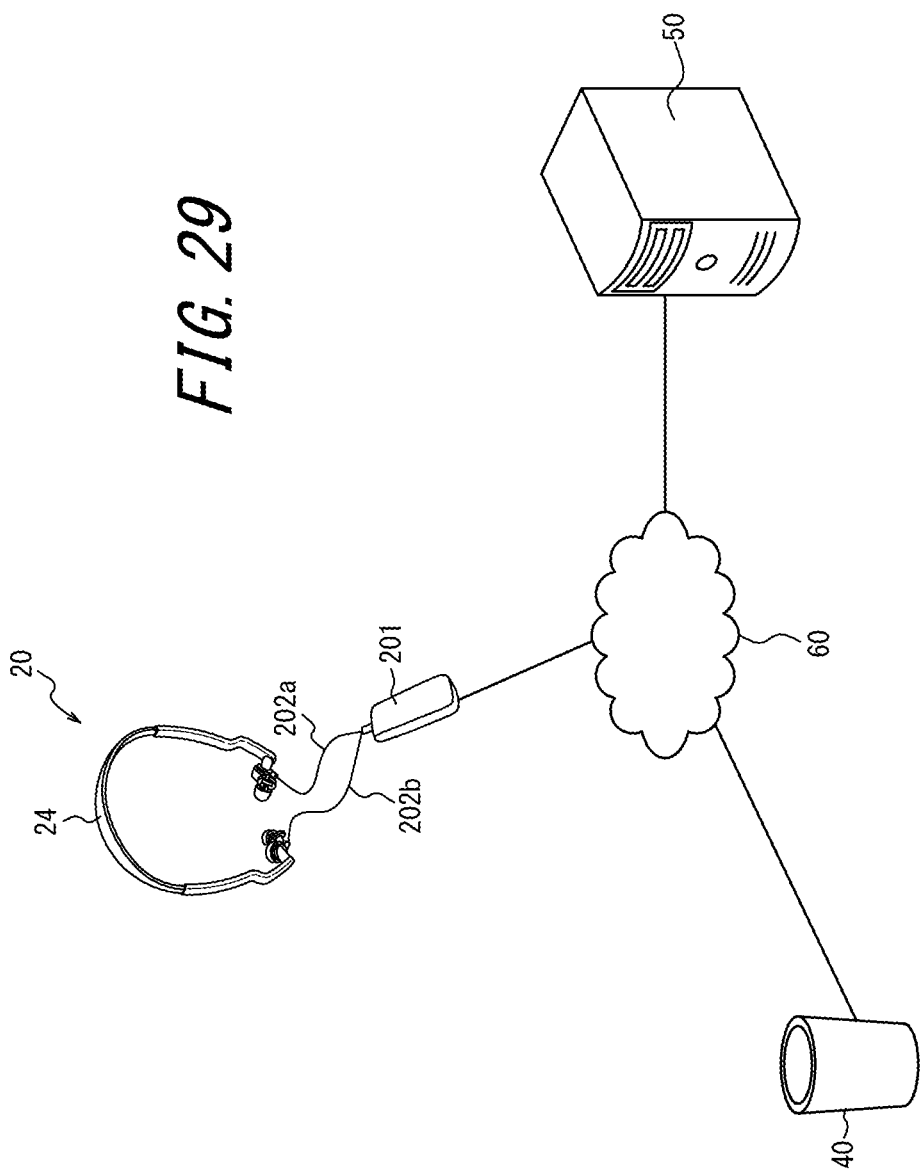
FIG. 29 illustrates the configuration of another embodiment of a massage system 2 according to the present disclosure.

FIG. 29 schematically illustrates another embodiment of the massage system 2. The sleep assessment system 1 and the massage apparatus 40 may be connected directly to the network 60, as illustrated in FIG. 29. In this case, the control to be executed by the information processing apparatus 10 may be executed by the server 50. Similar effects to those of the system illustrated in FIG. 25 can be achieved by the system illustrated in FIG. 29.

Figure 30:
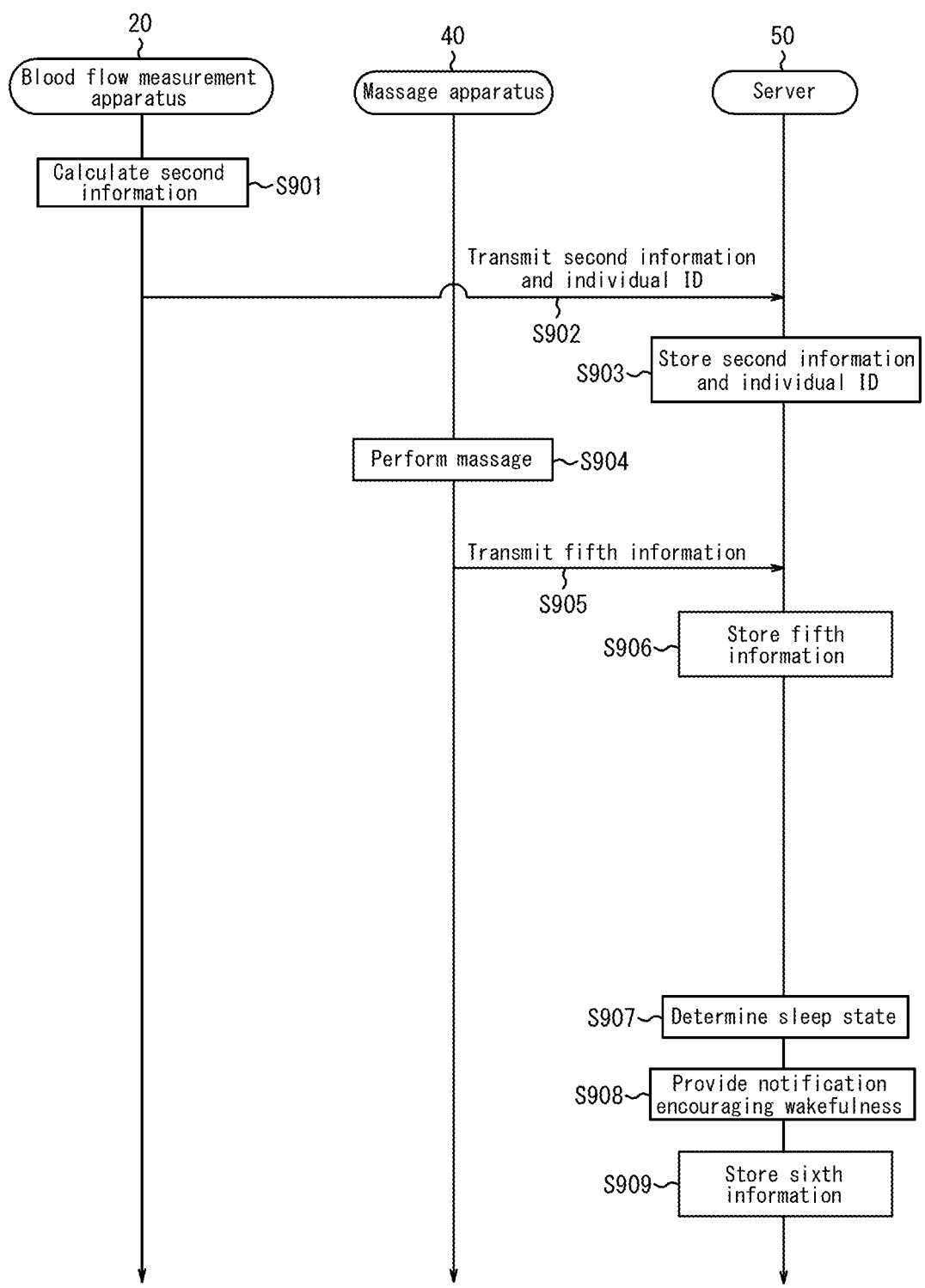
FIG. 30 is a sequence diagram illustrating an example of a control procedure of the massage system 2 of FIG. 29.

Next, with reference to FIG. 30, the processing executed by the server 50 illustrated in FIG. 29 is described. FIG. 30 is a sequence diagram illustrating an example of a control procedure of the massage system 2 of FIG. 29.

The blood flow measurement apparatus 20 calculates the second information (step S901).

The blood flow measurement apparatus 20 transmits the second information and the individual ID to the server 50 (step S902).

The server 50 stores the second information and the individual ID (step S903).

The massage apparatus 40 performs the massage (step S904).

The massage apparatus 40 transmits the fifth information to the server 50 (step S905).

The server 50 stores the fifth information (step S906).

The server 50 determines the sleep state (step S907).

The server 50 provides notification encouraging wakefulness (step S908).

The server 50 stores the sixth information (step S909).

Other Embodiment

Figure 31:
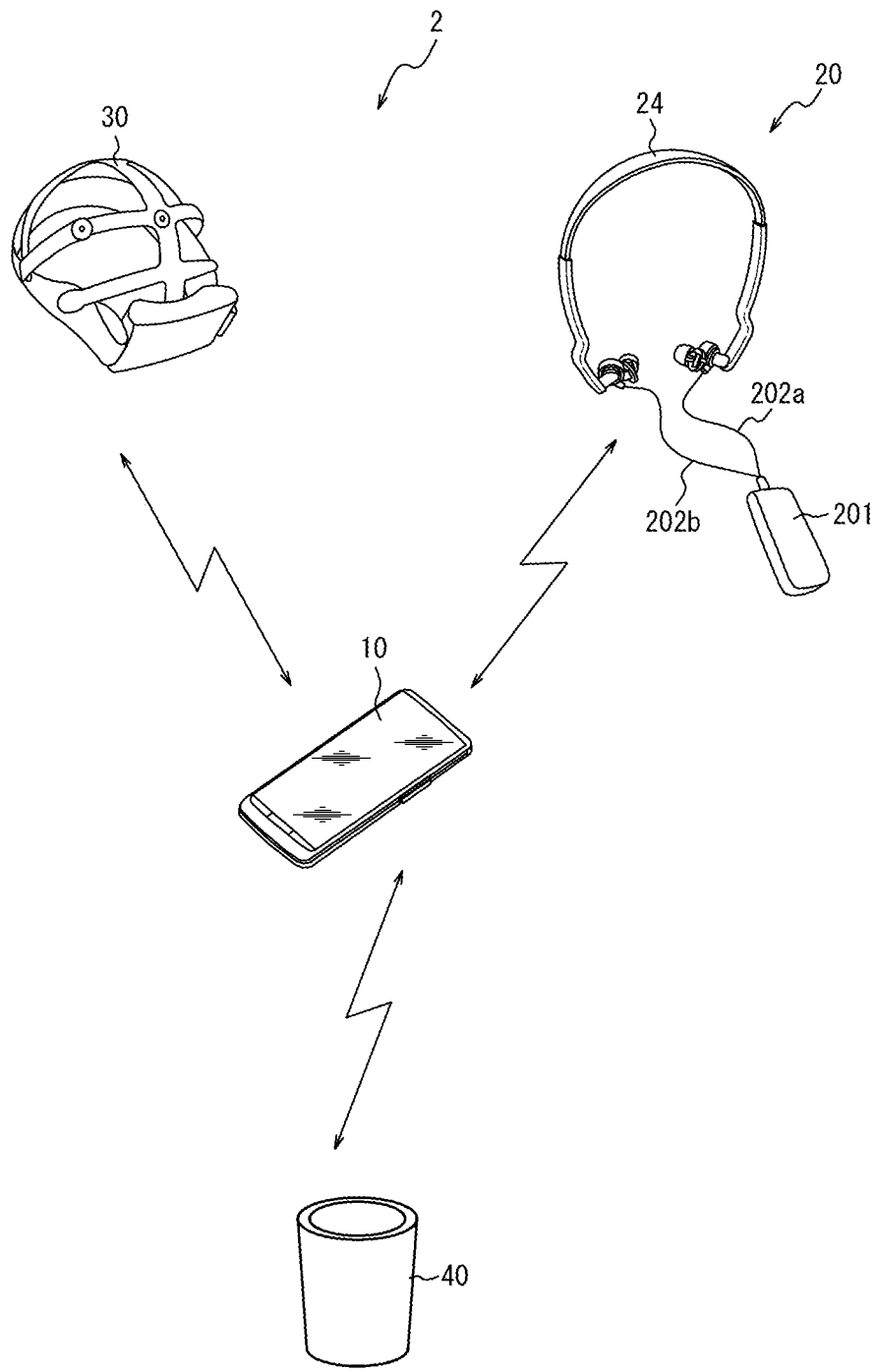
FIG. 31 illustrates the configuration of another embodiment of a massage system 2 according to the present disclosure.
Figure 32:
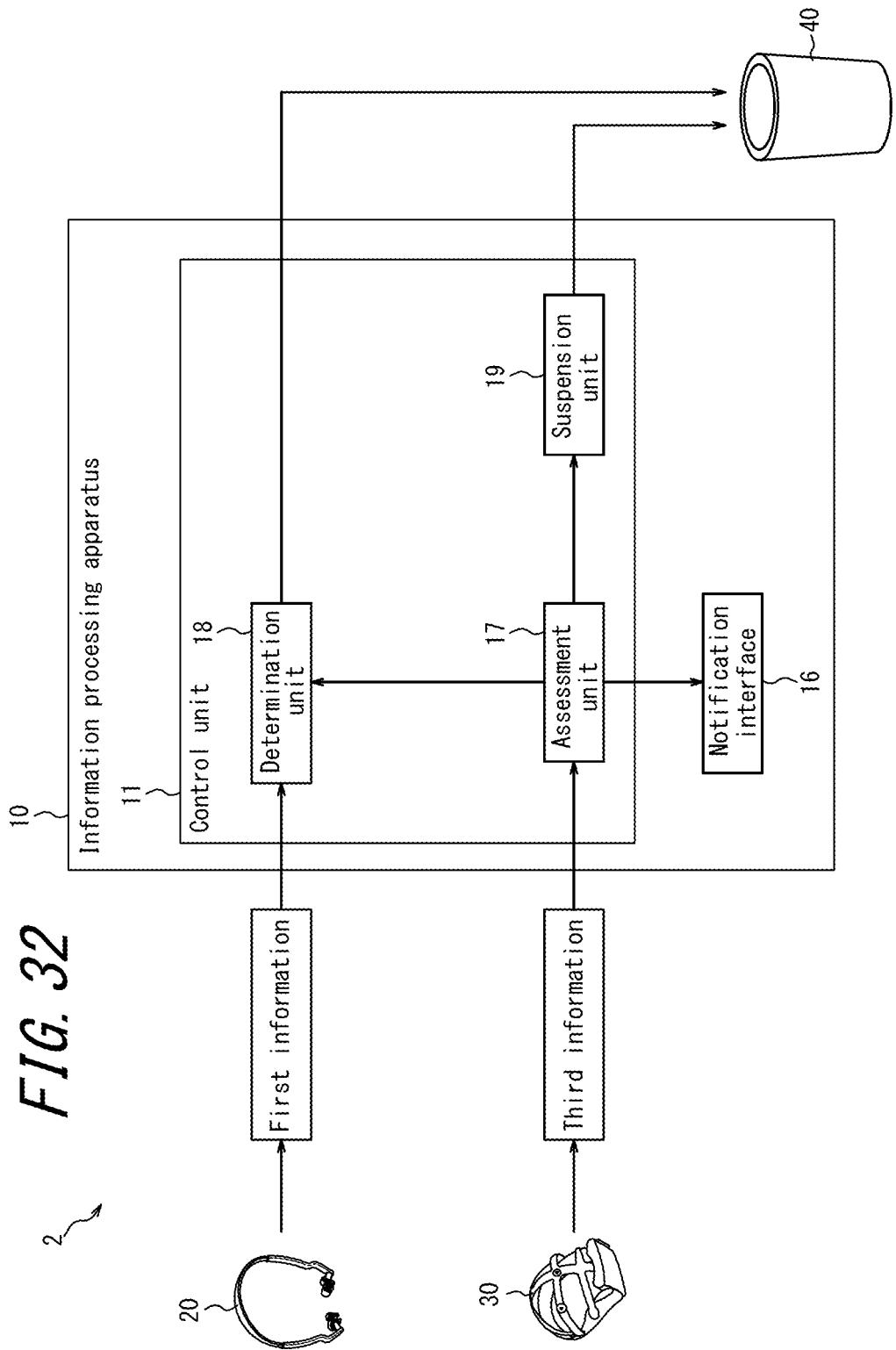
FIG. 32 is a schematic view illustrating the functions of an information processing apparatus 10 of FIG. 31.

FIG. 31 schematically illustrates the configuration of another embodiment of the massage system 2 according to FIG. 17. FIG. 32 is a schematic view illustrating the functions of the information processing apparatus 10 of FIG. 31. In this other embodiment, the massage system 2 includes the brain wave measurement apparatus 30.

Figure 33:
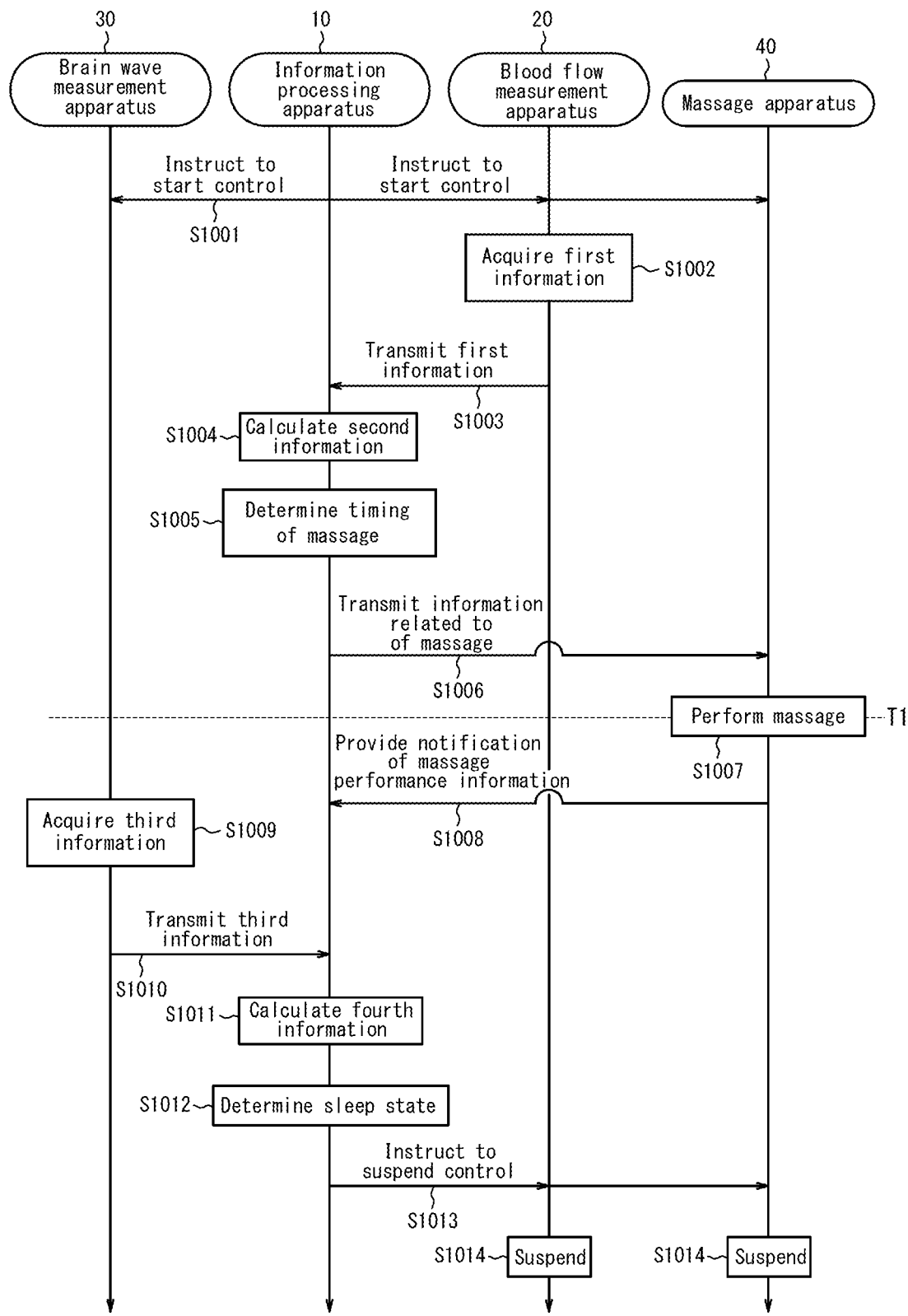
FIG. 33 is a sequence diagram illustrating an example of a control procedure at the time of sleep onset support by the massage system 2 of FIG. 31.

FIG. 33 is a sequence diagram illustrating an example of a control procedure for sleep onset support by the massage system 2 illustrated in FIG. 31. The sequence illustrated in FIG. 13 may, for example, be started when the user wears the massage apparatus 40, the brain wave measurement apparatus 30, and the blood flow measurement apparatus 20 and provides operation input to start control on the information processing apparatus 10.

The information processing apparatus 10 transmits a signal instructing to start control to the massage apparatus 40, the brain wave measurement apparatus 30, and the blood flow measurement apparatus 20 based on operation input from the user (step S1001). The massage apparatus 40, the brain wave measurement apparatus 30, and the blood flow measurement apparatus 20 each begin operating upon receiving the signal, from the information processing apparatus 10, instructing to start control.

The blood flow measurement apparatus 20 acquires the first information (step S1002).

The blood flow measurement apparatus 20 transmits the acquired first information to the information processing apparatus 10 (step S1003).

The information processing apparatus 10 determines the timing of the massage based on the first information received from the blood flow measurement apparatus 20 (step S1005). For example, the information processing apparatus 10 determines the timing of pressure application.

The information processing apparatus 10 transmits information related to the determined timing of the massage to the massage apparatus 40 (step S1006).

The massage apparatus 40 performs the massage at the timing acquired from the information processing apparatus 10, i.e. at the timing synchronized with the pulse wave (step S1007). For example, the massage apparatus 40 performs the massage in synchronization with the timing of the e wave. Specifically, the control unit 41 drives the actuators 48 in conjunction with the timing of the e wave, for example. It becomes easier for the blood flow to be pushed towards the heart accurately, facilitating efficient blood circulation, by the control unit 41 driving the actuators 48 in synchronization with the timing at which the acceleration pulse wave becomes the e wave.

The control unit 41 may drive the four actuators 48*a*, 48*b*, 48*c*, 48*d* at different timings. For example, the control unit 41 may drive the actuators 48*a*, 48*b*, 48*c*, 48*d* in this order at the timing of diastole. When the actuators 48 are driven in order from the distal end in this way, the calf is pressed in order from the distal side towards the heart side, making it easier to push blood towards the heart side.

The massage apparatus 40 notifies the information processing apparatus 10 of massage performance information (step S1008). The massage performance information includes the start time of the massage, the type and intensity of the massage, and the like.

Step S1002 through step S1008 may be executed repeatedly. Performance of the massage makes it easier to increase the circulating blood volume that returns to the user's heart. When the circulating blood volume increases, the stroke volume (SV) of blood pumped from the heart to the whole body per heartbeat increases. By Starling's law, the user's brain stimulates the parasympathetic nerves when the SV increases. Stimulation of the parasympathetic nerves makes it easier for the user to relax. Consequently, the user can fall asleep more easily. Execution of steps S1002 through S1008 by the massage apparatus 40 in this way facilitates induction of sleep onset in the user.

The brain wave measurement apparatus 30 acquires the third information at the brain wave measurement unit 34 (step S1009).

The brain wave measurement apparatus 30 transmits the acquired third information to the information processing apparatus 10 (step S1010).

The information processing apparatus 10 calculates the fourth information based on the third information acquired from the brain wave measurement apparatus 30 (step S1011). The processing in step S1011 for the information processing apparatus 10 to acquire the third information by the control unit 31 of the brain wave measurement apparatus 30 may be executed at a time T1 at which the massage apparatus 40 performed the massage, or at any point in time after S1007.

The information processing apparatus 10 determines the sleep state of the user based on the fourth information (step S1012). Specifically, the information processing apparatus 10 determines whether the user has fallen asleep.

The information processing apparatus 10 transmits a signal instructing to suspend control to the massage apparatus 40 and the blood flow measurement apparatus 20 when it is determined that the user has fallen asleep (step S1013).

The massage apparatus 40 and the blood flow measurement apparatus 20 suspend control upon receiving the signal, from the information processing apparatus 10, for suspending control (step S1014).

In response to the signal instructing to suspend control, the massage apparatus 40 and the blood flow measurement apparatus 20 suspend operations when it is determined that the user has fallen asleep. It is therefore unnecessary for the user to provide operation input himself to suspend operations of the massage apparatus 40 and the blood flow measurement apparatus 20. When, for example, a timer is set in advance, the information processing apparatus 10 may suspend operations of the massage apparatus 40 and the blood flow measurement apparatus 20 after the set predetermined time elapses, even if the user has not fallen asleep.

When the user has not fallen asleep, steps S1009 through S1012 may be repeated.

Figure 34:
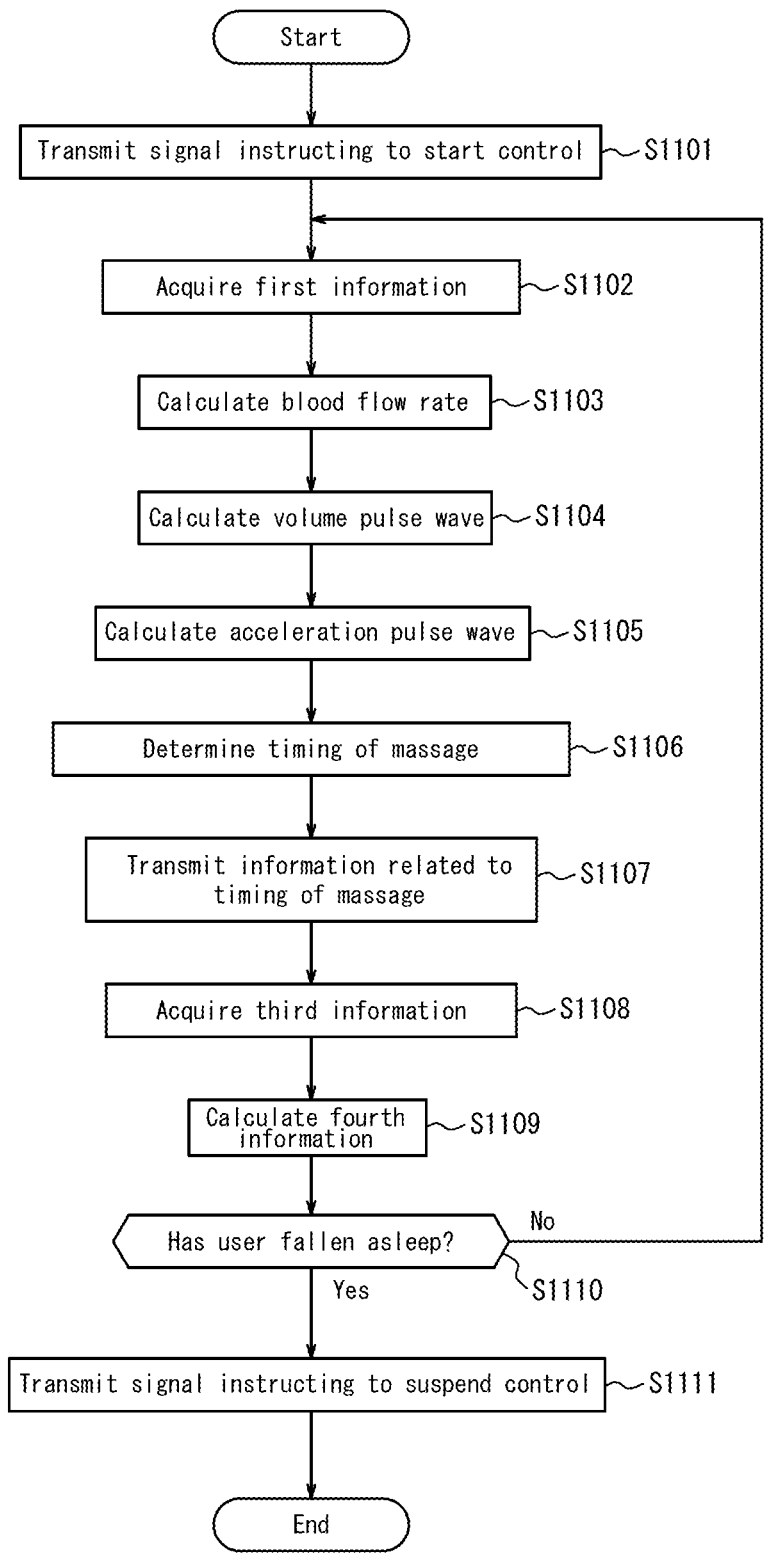
FIG. 34 is a flowchart illustrating the example of the control procedure by the information processing apparatus 10 of FIG. 33 in greater detail.

FIG. 34 is a flowchart illustrating an example of processing executed by the information processing apparatus 10 during the control for sleep onset support of FIG. 33. The flowchart in FIG. 34 specifically illustrates processing executed by the control unit 11.

The information processing apparatus 10 transmits a signal instructing to start control to the massage apparatus 40, the brain wave measurement apparatus 30, and the blood flow measurement apparatus 20 based on operation input from the user (step S1101). The massage apparatus 40, the brain wave measurement apparatus 30, and the blood flow measurement apparatus 20 each begin control in response to the signal instructing to start control.

The information processing apparatus 10 acquires the first information from the blood flow measurement apparatus 20 (step S1102).

The information processing apparatus 10 calculates the blood flow rate based on the acquired first information (step S1103). The information processing apparatus 10 can calculate the blood flow rate using the Doppler shift, as described above.

The information processing apparatus 10 calculates the volume pulse wave, an example of which is illustrated in FIG. 16A, based on the calculated blood flow rate (step S1104). In other words, the information processing apparatus 10 calculates the volume pulse wave by treating the calculated blood flow rate as being proportional to the change in blood vessel thickness (blood vessel diameter), which becomes the volume pulse wave.

The information processing apparatus 10 calculates the acceleration pulse wave, an example of which is illustrated in FIG. 16B, by differentiating the calculated volume pulse wave twice over time (step S1105).

The information processing apparatus 10 determines the timing of the massage based on the acceleration pulse wave (step S1106). For example, the information processing apparatus 10 calculates the timing of the e wave in the acceleration pulse wave and determines to perform the massage in synchronization with the timing of the e wave. At this time, the information processing apparatus 10 may determine the timing of the massage taking into consideration the positional relationship between the body part where the blood flow was measured and the body part where the massage is to be performed.

The information processing apparatus 10 transmits information related to the determined timing of the massage to the massage apparatus 40 (step S1107). The massage apparatus 40 performs the massage based on the information related to the timing of the massage.

The information processing apparatus 10 acquires the third information from the brain wave measurement apparatus 30 (step S1108).

The information processing apparatus 10 calculates the fourth information based on the acquired third information (step S1109).

The information processing apparatus 10 determines whether the user has fallen asleep based on the calculated fourth information (step S1110). For example, the information processing apparatus 10 can determine whether the user has fallen asleep based on whether the θ waves are dominant with respect to α waves in the brain waves among the fourth information.

When determining that the user has not fallen asleep (step S1110: No), the information processing apparatus 10 may transition to step S1102 and repeat steps S1102 to S1110. When, for example, the α waves are dominant relative to the θ waves, the information processing apparatus 10 may determine that the user has not fallen asleep.

When it is determined that the user has fallen asleep (step S1110: Yes), the information processing apparatus 10 transmits a signal instructing to suspend control to the massage apparatus 40 and the blood flow measurement apparatus 20 (step S1111). When, for example, the θ waves are dominant relative to the α waves, the information processing apparatus 10 may determine that the user has fallen asleep. In response to the signal instructing to suspend control, the massage apparatus 40 and the blood flow measurement apparatus 20 suspend control.

The massage system 2 may be a system for supporting wakefulness based on the user's sleep stage when, for example, the user is taking a short nap of approximately 15 to 30 minutes. In this case, the blood flow measurement apparatus 20 may, for example, include the speaker 126 described in an embodiment of the sleep assessment system 1. The information processing apparatus 10 may include the notification interface 16 described in an embodiment of the sleep assessment system 1. The control of the information processing apparatus 10 when determining the sleep state may be similar to that of the sleep assessment system 1. The control may also be similar when the sleep assessment system 1 includes the brain wave measurement apparatus 30.

In the present disclosure, the massage apparatus 40 may be used individually or may be used in combination with a chair, desk, bed, massage chair, bench, cushion, bicycle, car, or any other apparatus, for example.

Figure 35:
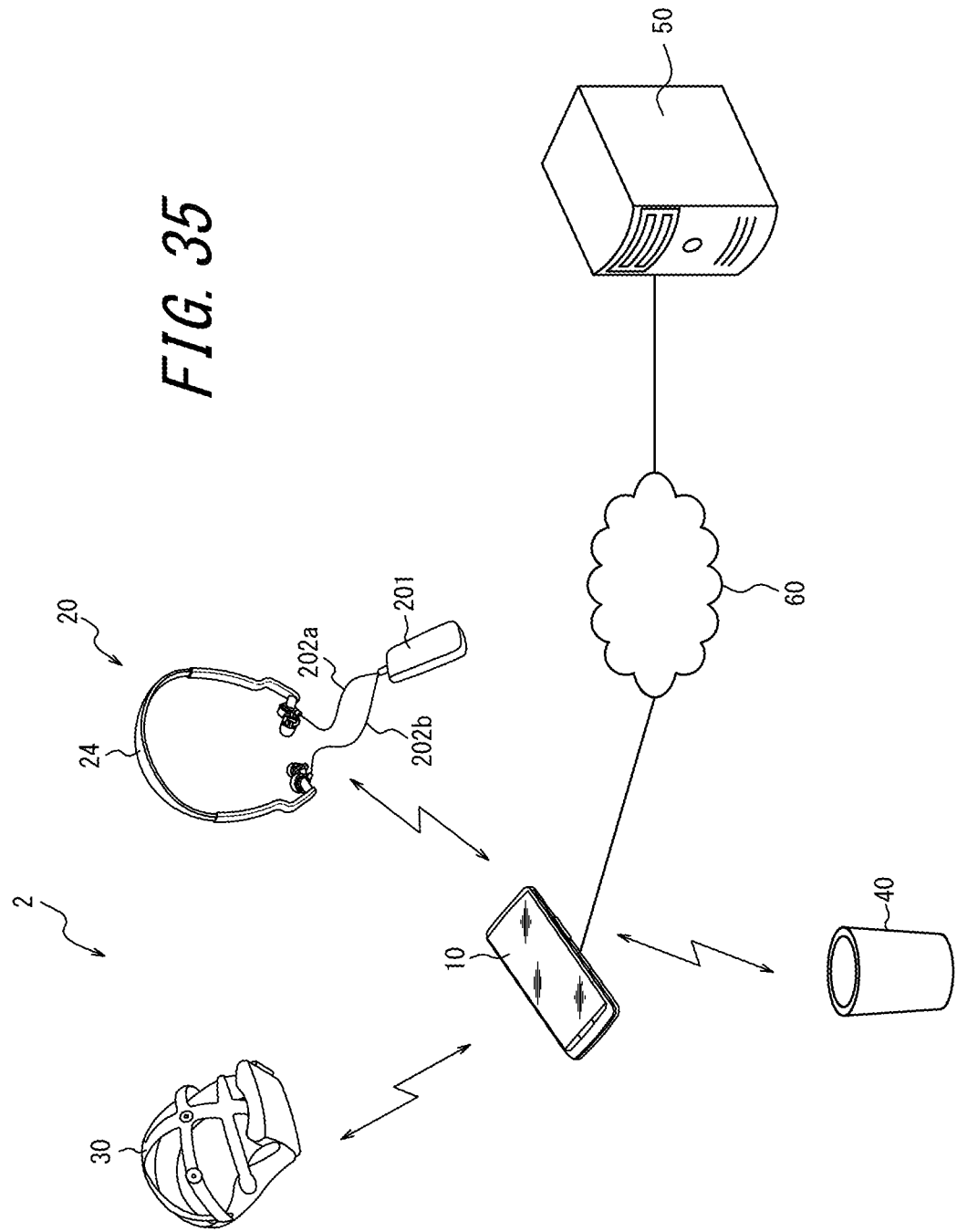
FIG. 35 schematically illustrates the configuration when the massage system 2 of FIG. 31 is connected to a server 50 over a network 60.

Next, the case of the massage system 2 illustrated in FIG. 31 being connected to a server over a network is described. FIG. 35 schematically illustrates the configuration when the massage system 2 is connected to a server 50 over a network 60. The connection between the server 50 and the information processing apparatus 10 and the internal configuration of the server 50 may be similar to those described in FIGS. 25 and 26.

Figure 36:
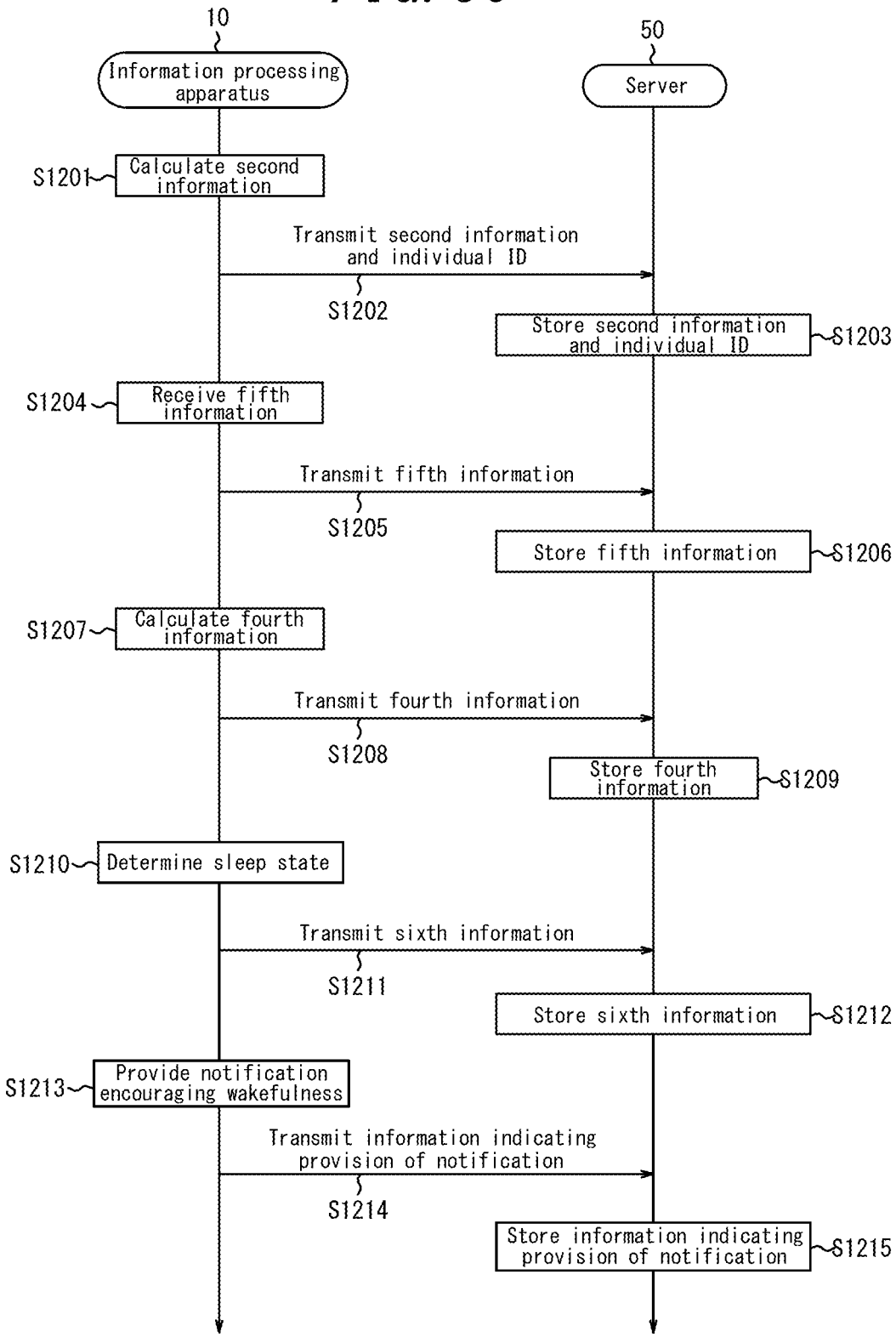
FIG. 36 is a sequence diagram illustrating an example of a control procedure of the massage system 2 of FIG. 35.

Here, with reference to FIG. 36, the operations of the system illustrated in FIG. 35 are described. FIG. 36 is a sequence diagram illustrating an example of a control procedure of the massage system 2 illustrated in FIG. 35.

The information processing apparatus 10 calculates the second information (step S1201).

The information processing apparatus 10 transmits the second information and the individual ID to the server 50 (step S1202).

The server 50 stores the second information and the individual ID (step S1203).

The information processing apparatus 10 receives the fifth information (step S1204).

The information processing apparatus 10 transmits the fifth information to the server 50 (step S1205).

The server 50 stores the fifth information (step S1206).

The information processing apparatus 10 calculates the fourth information (step S1207).

The information processing apparatus 10 transmits the fourth information to the server 50 (step S1208).

The server 50 stores the fourth information (step S1209).

The information processing apparatus 10 determines the sleep state (step S1210).

The information processing apparatus 10 transmits the sixth information to the server 50 (step S1211).

The server 50 stores the sixth information (step S1212).

The information processing apparatus 10 provides notification encouraging wakefulness (step S1213).

The information processing apparatus 10 transmits information indicating provision of notification to the server 50 (step S1214).

The server 50 stores the information indicating provision of notification (step S1215).

Figure 37:
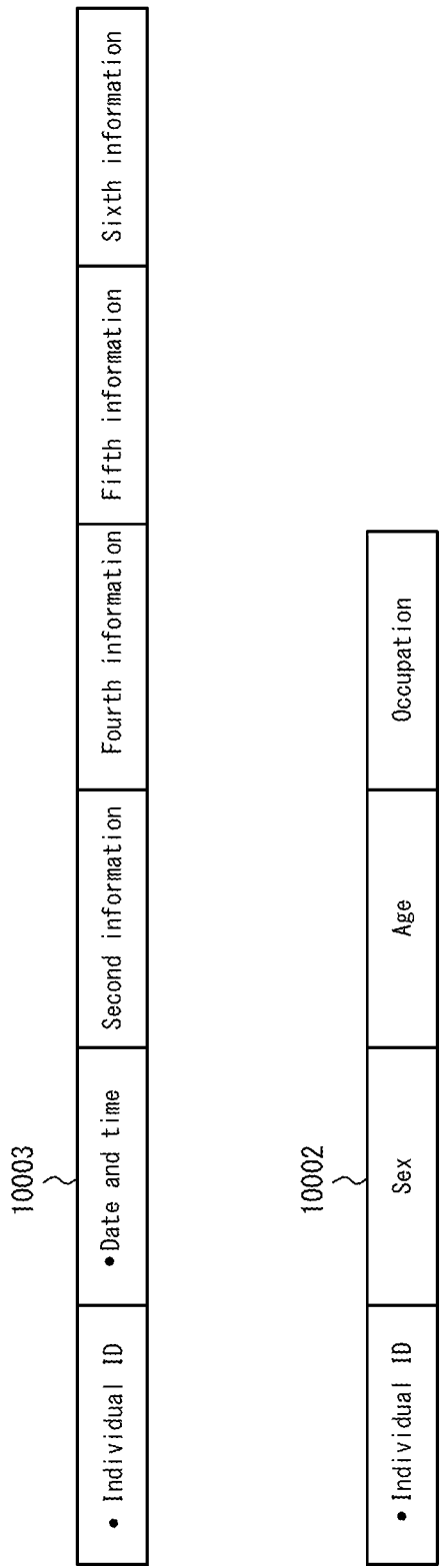
FIG. 37 is a conceptual diagram of the data structure of data stored on the server 50 in the massage system 2 of FIG. 35.

FIG. 37 is a conceptual view of the data stored on the server 50 in the massage system 2 illustrated in FIG. 35. In this case, information 10003 containing the second information, the fourth information, the fifth information, and the sixth information, with an individual ID and a date and time as primary keys, is stored in the storage 52 of the server 50.

Other Embodiment

Figure 38:
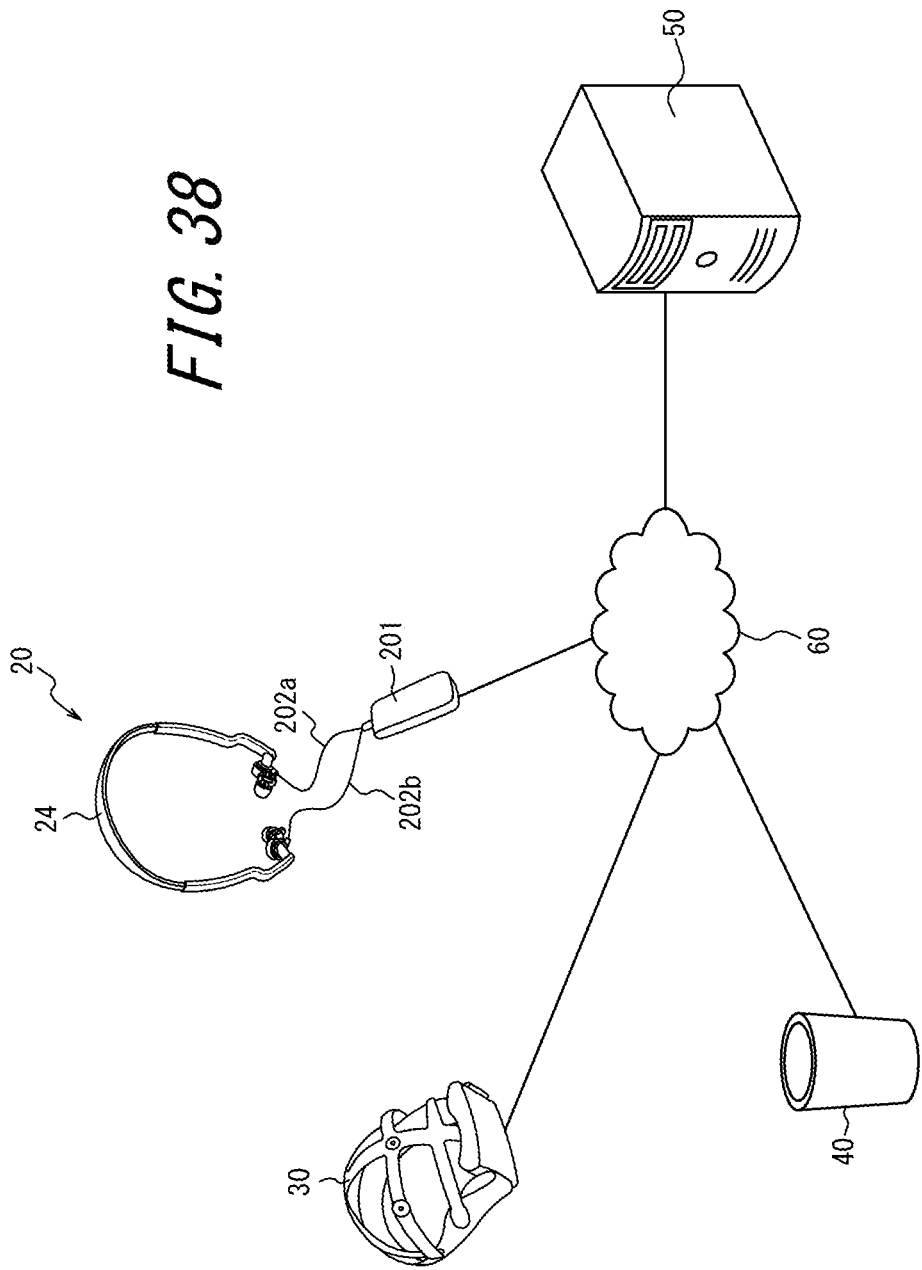
FIG. 38 illustrates the configuration of another embodiment of a massage system 2 according to the present disclosure.

FIG. 38 schematically illustrates another embodiment of the massage system 2. In this case, the brain wave measurement apparatus 30 may be connected directly to the network 60. Similar effects to those of the system illustrated in FIG. 35 can be achieved by the system illustrated in FIG. 38.

Figure 39:
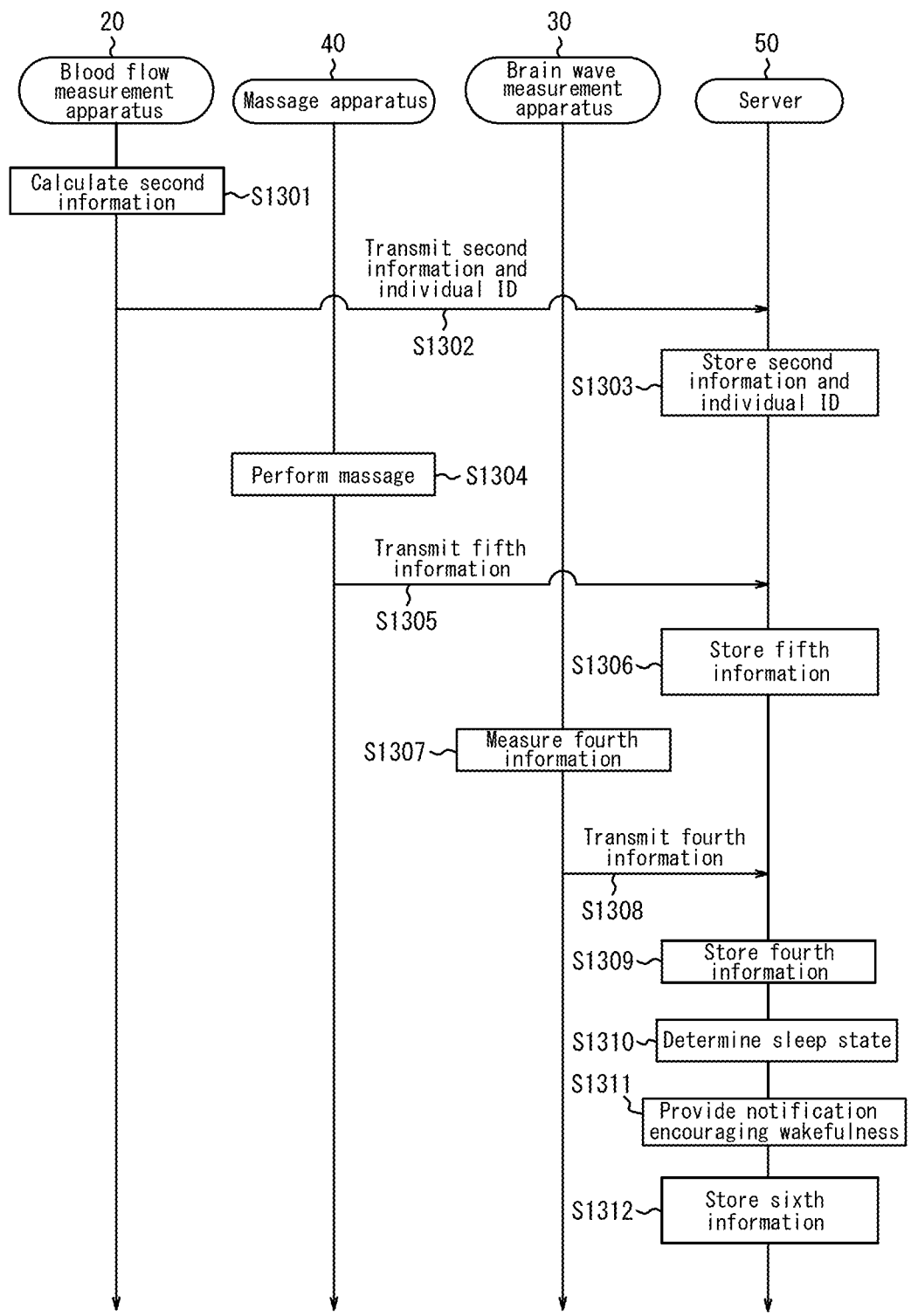
FIG. 39 is a sequence diagram illustrating an example of a control procedure of the massage system 2 of FIG. 38.

Here, with reference to FIG. 39, the processing executed by the server 50 illustrated in FIG. 38 is described. FIG. 39 is a sequence diagram illustrating an example of a control procedure by the massage system 2 illustrated in FIG. 38.

The blood flow measurement apparatus 20 calculates the second information (step S1301).

The blood flow measurement apparatus 20 transmits the second information and the individual ID to the server 50 (step S1302).

The server 50 stores the second information and the individual ID (step S1303).

The massage apparatus 40 performs the massage (step S1304).

The massage apparatus 40 transmits the fifth information to the server 50 (step S1305).

The server 50 stores the fifth information (step S1306).

The brain wave measurement apparatus 30 measures the fourth information (step S1307).

The brain wave measurement apparatus 30 transmits the fourth information to the server 50 (step S1308).

The server 50 stores the fourth information (step S1309).

The server 50 determines the sleep state (step S1310).

The server 50 provides notification encouraging wakefulness (step S1311).

The server 50 stores the sixth information (step S1312).

The present disclosure is not limited to the above embodiments. A variety of changes and improvements may be made without departing from the spirit and scope of the present disclosure.

For example, in the above embodiments, the information processing apparatus 10, blood flow measurement apparatus 20, brain wave measurement apparatus 30, and massage apparatus 40 have been described as being included separately in the massage system 2. The information processing apparatus 10, blood flow measurement apparatus 20, and brain wave measurement apparatus 30 may, however, be mounted in a chair-type massage apparatus 40, for example.

(Electronic Device)

The aforementioned sleep assessment system 1 or massage system 2 may be combined with any electronic device and used as a function of the electronic device. For example, the information processing apparatus 10 may be an information device or information terminal such as a personal computer, a smartphone, or a tablet. The blood flow measurement apparatus 20 may, for example, be used as an earphone or headphone. In other words, the blood flow measurement unit 24 of the blood flow measurement apparatus 20 may, for example, be disposed inside an earphone or headphone.

(Control Method)

The control of functional components executed by the control unit in the sleep assessment system 1 and the massage system 2 may be used as a control method of a program.

Various embodiments have been described above for a clear disclosure. The appended claims, however, are not limited to the above embodiments and are to be construed as encompassing all of the possible modifications and alternate configurations that a person of ordinary skill in the art could make within the scope of the fundamental features illustrated in the present disclosure. The subject matter of the various embodiments may also be freely combined. For example, the blood flow rate, blood flow wave height, volume pulse wave, and acceleration pulse wave may be calculated by a blood flow measurement apparatus. The brain waves may be calculated by a brain wave measurement apparatus.

The invention claimed is:

1. A massage system comprising:
a massager for massaging a user; and
a sleep assessment system comprising:
an optical emitter configured to emit light;
an optical detector configured to detect the light and acquire first biological information related to blood flow of the user; and
a controller configured to:
determine a sleep stage of the user based on the first biological information, calculate a pulse wave of the user based on the first biological information, and control the massager to perform a massage at a timing synchronized with the pulse wave of the user.

2. The massage system of claim 1, further comprising:

a storage configured to store second biological information related to brain waves;

wherein the controller is configured to determine the sleep stage of the user based on the first biological information and the second biological information.

3. The massage system of claim 1, further comprising a notification interface configured to provide notification to awaken the user.

4. The massage system of claim 1, wherein the controller is configured to determine the timing of the massage based on a positional relationship between a first site of the user where the first biological information is acquired and a second site of the user where the massage is to be performed.

5. The massage system of claim 1, wherein the controller is further configured to determine sleep onset of the user and to control driving of the massage.

6. The massage system of claim 5, wherein the controller is configured to suspend control of the massager unit when it is determined that sleep onset of the user has occurred.

7. The massage system of claim 1, wherein the timing synchronized with the pulse wave of the user is a timing at which an acceleration pulse wave becomes an e wave.

8. An electronic device comprising the sleep assessment system of claim 1.

9. A control method executed by a controller in a massage system comprising:

emitting light;

detecting light;

acquiring first biological information related to blood flow of a user;

determining a sleep stage of the user based on the first biological information;

calculating a pulse wave of the user based on the first biological information; and controlling the massager to perform a massage at a timing synchronized with the pulse wave of the user.

10. The control method of claim 9, further comprising:

preparing second biological information related to brain waves;

wherein the sleep stage of the user is determined based on the first biological information and the second biological information.

11. The control method of claim 9, further comprising determining a timing of a massage for the user based on the first biological information.

12. The control method of claim 11, further comprising determining the timing of the massage based on a positional relationship between a first site of the user where the first biological information is measured and a second site of the user where the massage is to be performed.

13. The control method of claim 11, further comprising:

determining sleep onset and wakefulness of the user, in addition to the sleep stage, based on the first biological information; and controlling driving of the massage based on the determining.

14. The control method of claim 13, wherein the controlling comprises suspending the massage when it is determined that sleep onset has occurred.

15. The control method of claim 9, further comprising providing notification to awaken the user.

16. The control method of claim 9, wherein the timing synchronized with the pulse wave of the user is a timing at which an acceleration pulse wave becomes an e wave.

* * * * *